(12) United States Patent
Li et al.

(10) Patent No.: US 10,094,793 B2
(45) Date of Patent: Oct. 9, 2018

(54) NANOMATERIAL-BASED PHOTOTHERMAL IMMUNOSENSING FOR QUANTITATIVE DETECTION OF DISEASE BIOMARKERS

(71) Applicants: XiuJun Li, El Paso, TX (US); Guanglei Fu, El Paso, TX (US)

(72) Inventors: XiuJun Li, El Paso, TX (US); Guanglei Fu, El Paso, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/269,301

(22) Filed: Sep. 19, 2016

(65) Prior Publication Data

US 2017/0082615 A1    Mar. 23, 2017

Related U.S. Application Data

(60) Provisional application No. 62/220,974, filed on Sep. 19, 2015.

(51) Int. Cl.
*G01N 25/48* (2006.01)
*G01N 33/58* (2006.01)

(52) U.S. Cl.
CPC ......... *G01N 25/4813* (2013.01); *G01N 33/58* (2013.01); *G01N 33/583* (2013.01); *G01N 33/587* (2013.01)

(58) Field of Classification Search
CPC .. G01N 25/4813; G01N 33/58; G01N 33/583; G01N 33/587
See application file for complete search history.

(56) References Cited

U.S. PATENT DOCUMENTS

| 4,920,046 A | 4/1990 | McFarland ............... 435/7.31 |
| 5,439,830 A * | 8/1995 | Sakashita ............ G01N 21/171 435/962 |
| 5,798,273 A | 8/1998 | Shuler et al. ............ 436/514 |
| 5,998,221 A | 12/1999 | Malick et al. ........... 436/514 |
| 6,194,220 B1 | 2/2001 | Malick et al. ........... 436/514 |
| RE38,430 E | 2/2004 | Rosenstein ............. 436/514 |
| 7,052,831 B2 | 5/2006 | Fletcher et al. ........... 435/5 |

OTHER PUBLICATIONS

Bahmani et al., "Erythrocyte-derived photo-theranostic agents: hybrid nano-vesicles containing indocyanine green for near infrared imaging and therapeutic applications," Sci. Rep. vol. 3, 2013, #2180, 7 pages.
Barbosa et al., "A lab-in-a-briefcase for rapid prostate specific antigen (PSA) screening from whole blood." Lab Chip, vol. 14, No. 16, 2014, pp. 2918-2928.
Chen et al., "Ultrasensitive electrochemical detection of prostate-specific antigen by using antibodies anchored on a DNA nanostructural scaffold." Anal. Chem. vol. 86, No. 15, 2014, pp. 7337-7342.
Cheng et al., "PEGylated Micelle Nanoparticles Encapsulating a Non-Fluorescent Near-Infrared Organic Dye as a Safe and Highly-Effective Photothermal Agent for In Vivo Cancer Therapy," Adv. Funct. Mater. vol. 23, No. 47, 2013, pp. 5893-5902.
Choi et al., "A novel Au-nanoparticle biosensor for the rapid and simple detection of PSA using a sequence-specific peptide cleavage reaction ," Biosens. Bioelectron., vol. 49, 2013, pp. 415-419.
Fu et al. "Magnetic Prussian blue nanoparticles for targeted photothermal therapy under magnetic resonance imaging guidance." Bioconjugate Chem., vol. 25, No. 9, 2014, pp. 1655-1663.
Fu et al., "Prussian blue nanoparticles operate as a new generation of photothermal ablation agents for cancer therapy." Chem. Commun., vol. 48, No. 94, 2012, pp. 11567-11569.
Gao et al., "Enhanced Colorimetric Immunoassay Accompanying with Enzyme Cascade Amplification Strategy for Ultrasensitive Detection of Low-Abundance Protein," Sci. Rep., vol. 4, 2014, #3966, 8 pages.
Hu et al., "Synthesis of Prussian blue nanoparticles with a hollow interior by controlled chemical etching." Angew. Chem. Int. Edit., 51, No. 4, 2012, pp. 984-988.
Jaetao et al., "Enhanced Leukemia Cell Detection Using a Novel Magnetic Needle and Nanoparticles ," Cancer Res. vol. 69, No. 21, 2009, pp. 8310-8316.
Ke et al., "Gold-nanoshelled microcapsules: a theranostic agent for ultrasound contrast imaging and photothermal therapy." Angew. Chem. Int. Edit. vol. 50, No. 13, 2011, pp. 3017-3021.
Lee et al., "Two-dimensional Layered MoS2 Biosensors Enable Highly Sensitive Detection of Biomolecules ," Sci. Rep. vol. 4, 2014, #7352, 7 pages.
Liu et al., "A dual-functional electrochemical biosensor for the detection of prostate specific antigen and telomerase activity." Chem. Commun. vol. 49, No. 59, 2013, pp. 6602-6604.
Moon et al., "In vivo near-infrared mediated tumor destruction by photothermal effect of carbon nanotubes." ACS Nano. vol. 3, No. 11, 2009, pp. 3707-3713.
Shan et al., "Upconverting Organic Dye Doped Core-Shell Nano-Composites for Dual-Modality NIR Imaging and Photo-Thermal Therapy ," Theranostics, vol. 3, No. 4, 2013, pp. 267-274.
Shokouhimehr et al., "Biocompatible Prussian blue nanoparticles: Preparation, stability, cytotoxicity, and potential use as an MRI contrast agent," Inorg. Chem. Commun., vol. 13, No. 1, 2010, pp. 58-61.
Shokouhimehr et al., "Dual purpose Prussian blue nanoparticles for cellular imaging and drug delivery: a new generation of $T_1$-weighted MRI contrast and small molecule delivery agents." J. Mater. Chem., vol. 20, 2010, pp. 5251-5259.
Spence et al., "Activated photothermal heating using croconaine dyes," Chem. Sci. vol. 4, 2013, pp. 4240-4244.
Woo et al., "A Novel Colorimetric Immunoassay Utilizing the Peroxidase Mimicking Activity of Magnetic Nanoparticles," Int. J. Mol. Sci. vol. 14, No. 5, 2013, 9999-10014.

(Continued)

*Primary Examiner* — Tracy Vivlemore
*Assistant Examiner* — Carmencita M Belei
(74) *Attorney, Agent, or Firm* — Norton Rose Fulbright US LLP

(57) ABSTRACT

Certain embodiments of the invention are directed to a photothermal immunoassay employing a thermometer or colorimetric detection method for sensitive quantitative readout based on the photothermal effect provided by a detection reagent.

7 Claims, 14 Drawing Sheets

(56) References Cited

OTHER PUBLICATIONS

Wu et al., "Hybrid polypeptide micelles loading indocyanine green for tumor imaging and photothermal effect study." Biomacromolecules. vol. 14, No. 9, 2013, pp. 3027-3033.
Yu et al., "The artificial peroxidase activity of magnetic iron oxide nanoparticles and its application to glucose detection," Biomaterials, vol. 30, No. 27, 2009, pp. 4716-4722.
Zhang et al., "Prussian blue modified iron oxide magnetic nanoparticles and their high peroxidase-like activity," J. Mater. Chem., vol. 20, 2010, pp. 5110-5116.
Zheng et al., "Single-step assembly of DOX/ICG loaded lipid--polymer nanoparticles for highly effective chemo-photothermal combination therapy." ACS Nano, vol. 7, No. 3, 2013, pp. 2056-2067.

\* cited by examiner

| Serum sample number | Standard PSA concentration (ng·mL$^{-1}$) | Color changes | UV-Vis detection result (ng·mL$^{-1}$) | Recovery (%) |
|---|---|---|---|---|
| Control | 0 |  | | |
| No. 1 | 4.0 |  | 3.65±0.20 | 91.3±5.0 |
| No. 2 | 8.0 |  | 7.32±0.36 | 91.6±4.6 |
| No. 3 | 16.0 |  | 14.9±0.90 | 93.1±5.7 |

| Serum sample Number | Standard PSA concentration (ng·mL⁻¹) | Temperature increase (°C) | Measured PSA concentration (ng·mL⁻¹) | Recovery (%) |
|---|---|---|---|---|
| 1 | 4.0 | 8.1±0.6 | 3.67±0.18 | 91.7±4.4 |
| 2 | 8.0 | 15.6±0.7 | 7.70±0.46 | 96.3±5.8 |
| 3 | 16.0 | 22.5±0.8 | 15.30±0.99 | 95.8±6.2 |

NANOMATERIAL-BASED PHOTOTHERMAL IMMUNOSENSING FOR QUANTITATIVE DETECTION OF DISEASE BIOMARKERS

PRIORITY

This Application claims priority to U.S. Application No. 62/220,974 filed Sep. 19, 2015, which is incorporated herein by reference in its entirety.

BACKGROUND OF THE INVENTION

1. Field of the Invention

The present invention relates generally to the field of medicine and disease diagnosis. More particularly, it concerns kits and devices for detecting disease using a photothermal immunoassay.

2. Description of Related Art

Immunoassay technology provides a simple and relatively rapid means for determining the presence or absence of analytes in biological samples. The information provided from immunoassay diagnostic tests are often critical to patient care. Assays are typically performed to detect qualitatively or quantitatively the presence of particular analytes, for example, antigens that are present when a human subject has a particular disease or condition Immunoassays practiced in the art are numerous, and include assays for diseases, such as infections caused by bacteria or viruses, or conditions, such as pregnancy.

The development of an immunoassay applicable for "point-of-care" (POC) detection has been the subject of great research interest in biomedical field especially for clinical diagnostics. Various immunoassays based on different detection principles such as the traditional ELISA, surface plasmon resonance, chemiluminescence, electrochemistry, and fluorescence methodologies have been developed for this purpose. Despite current research successes, these traditional immunoassays have been confronted with limitations to their further POC diagnostic applications. Typically, one of the most critical bottlenecks for developing POC detection is the analytical readout method because most traditional readout strategies are relying on bulky and expensive analytical equipment. In addition, professionally trained operators are generally indispensable, limiting their further application for widespread POC diagnosis. Therefore, the development of novel immunoassay with generally applicable readout methods has been increasingly desirable to meet the demand of modern clinical diagnostics.

SUMMARY OF THE INVENTION

The inventors have developed a photothermal immunoassay employing a thermometer for sensitive quantitative readout based on the photothermal effect provided by a detection reagent. In certain aspects, photothermal or thermogenic nanoparticles (NPs) captured in a sandwich immuno-detection system are detected by exposure of the photothermal nanomaterials to light of an appropriate wavelength, resulting in the production of heat. In certain aspects, iron oxide nanoparticles are used as the catalyst to produce a photothermal agent. In a further aspect, the iron oxide NPs are chemically transformed into a photothermal agent. In still further aspects, a photothermal agent can be coupled directly or indirectly to the nanoparticle. In certain aspects, the light used can have a wavelength between 100, 200, 300, 400, 500, 600, 700, 800 nm and 1,000, 1,500, 2,000, 3,000, 4,000, 5,000, 10,000 nm. In particular aspects the wavelength of light is between about 500 nm and 1000 nm.

In certain aspects, the photothermal effect of the $Fe_3O_4$ NPs-catalyzed 3,3',5,5'-tetramethylbenzidine (TMB)-$H_2O_2$ colorimetric system can be used with the charge transfer complex of the one-electron oxidation product of TMB (oxidized TMB) as the photothermal agent. In a further aspect, iron oxide nanoparticles can be transformed into photothermally effective Prussian blue (PB) NPs with the PB NPs as the photothermal agent. The photothermal agents can convert the detection signal into thermometer-detectable heat through the photothermal effect, thereby allowing the efficient quantitative readout with only a thermometer. In certain aspects, results can also be observed through visual color changes seen by the human eye or a spectrometer. The introduction of the photothermal strategy to realize the thermometer-based readout method opens up new horizons for POC diagnostics.

The photothermal agent is not particularly limited as long as it is able to convert energy of light into thermal energy. In certain aspects, a photothermal agent is a nanomaterial, dye, or pigment that absorb certain wavelengths of light and convert the absorbed light into heat. The dye may be, but is not limited to azo dyes, metal complex salt azo dyes, pyrazolone azo dyes, naphthoquinone dyes, anthraquinone dyes, phthalocyanine dyes, carbonium dyes, quinonimine dyes, methine dyes, cyanine dyes, squarylium pigments, pyrylium salts, and metal thiolate complex. Examples of pigments include, but are not limited to black pigments, yellow pigments, orange pigments, brown pigments, red pigments, violet pigments, blue pigments, green pigments, fluorescent pigments, metallic powder pigments, and other pigments such as polymer-binding pigments. Specifically, it is possible to use insoluble azo pigments, azo lake pigments, condensed azo pigments, chelate azo pigments, phthalocyanine type pigments, anthraquinone type pigments, perylene and perinone type pigments, thioindigo type pigments, quinacridone type pigments, dioxazine type pigments, isoindolinone type pigments, quinophthalone type pigments, dyed lake pigments, azine pigments, nitroso pigments, nitro pigments, natural pigments, fluorescent pigments, inorganic pigments, carbon black, or the like. In certain aspects the photothermal agent is iron oxide nanoparticles, Prussian blue nanoparticles, the charge transfer complex of the one-electron oxidation product of TMB (oxidized TMB), good nanorods, graphene oxide, carbon nanotubes, Indocyanine Green, CuS-based nanomaterials, or other photothermal nanomaterials.

The term "nanomaterial" as used herein, refers to particles comprising at least an iron oxide core or other materials with at least one dimension in the range of about 1 to about 1000 nanometers ("nm"). The nanomaterials of the invention may be of any shape. In certain embodiments the nanoparticles are spherical. The nanoparticles of the invention typically do not, but can, include a light-active molecule.

The nanomaterials of the invention may be chemically transformed to nanoparticles that enhance the conversion of light to heat. The surface of the nanoparticle may be coupled directly or indirectly with a light absorbing moiety. In some embodiments, the surface of the nanoparticle is treated or derivitized to permit attaching a ligand to the surface of the nanoparticle.

The phrase "increases the thermal activity of the nanomaterial" means exposure to a light source of the appropriate wavelength results in a nanoparticle providing increased signal or sensitivity when measured by color or heat in, for example, an immunoassay, as compared to a non-thermal active nanoparticle."

As used herein, "ligand" means a molecule of any type that will bind to an analyte of interest. For example and without limitation, in certain embodiments the ligand is an antibody, an antigen, a receptor, a nucleic acid, or an enzyme.

The term "analyte" as used herein refers to any substance of interest that one may want to detect using the invention, including but not limited to drugs, including therapeutic drugs and drugs of abuse; hormones; vitamins; proteins, including antibodies of all classes; peptides; steroids; bacteria; fungi; viruses; parasites; components or products of bacteria, fungi, viruses, or parasites; allergens of all types; products or components of normal or malignant cells; etc. As particular examples, there may be mentioned human chorionic gonadotropin (hCG); insulin; luteinizing hormone; organisms causing or associated with various disease states, such as *Streptococcus pyogenes* (group A), Herpes Simplex I and II, cytomegalovirus, Chlamydia, rubella antibody, influenza A and B; etc. In certain embodiments of the invention, the presence or absence of an analyte in a sample is determined qualitatively. In other embodiments, the amount or concentration of analyte in the sample is quantitatively determined.

The term "sample" as used herein refers to any biological sample that could contain an analyte for detection. In some embodiments, the biological sample is in liquid form, while in others it can be changed into a liquid form.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION

The inventors provide a solution to the need for easy to use detection devices for point of care (POC) detection and assay. The inventors describe herein a photothermal immunoassay that meets the needs of a POC device. The concept of photothermal conversion has emerged as a particularly attractive research topic in various fields because of the unique light-to-heat photo-physical conversion property. In particular, near-infrared (NIR) light-driven photothermal conversion has been intensively applied in biomedical field for photothermal therapy of cancers employing heat converted by photothermal agents from NIR light absorption.

In one aspect the photothermal immunoassay is based on the photothermal effect of the $Fe_3O_4$ NPs-catalyzed 3,3',5,5'-tetramethylbenzidine (TMB)-$H_2O_2$ colorimetric system. The $Fe_3O_4$ NPs-catalyzed charge transfer complex of the one-electron oxidation product of TMB (oxidized TMB) in the colorimetric immunosensing system was used as the near-infrared light-driven photothermal probe to convert the detection signal into heat through its photothermal effect, thereby allowing the sensitive detection of disease biomarkers with only a thermometer for analytical readout. In another aspect the iron oxide nanoparticle can be transformed in to a Prussian blue (PB)-nanomaterials that can convert the NIR light into heat. Heat generated from the photothermal conversion process can be accurately monitored by using a common thermometer, thus allowing for application in POC analysis due to the ease of a thermometer for portable, simple, and popularized analytical readout. Although photothermal effect of nanoparticles has been widely used for cancer therapy, the photothermal strategy has never been introduced for analytical applications especially for POC diagnostics.

Figure 1:
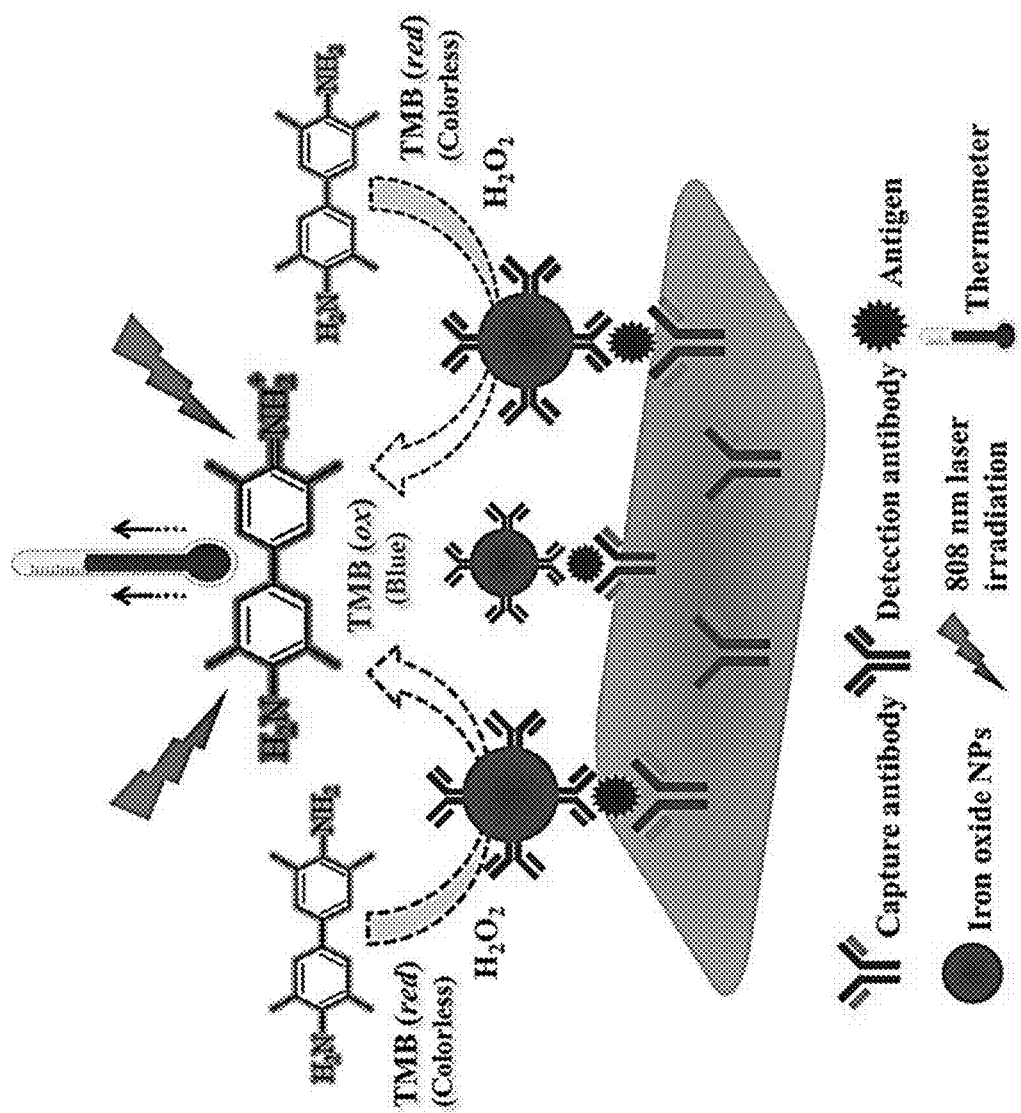
FIG. 1. Illustration of the photothermal immunosensing strategy based on the photothermal effect of the iron oxide NPs-catalyzed TMB-$H_2O_2$ colorimetric system.
Figure 2:
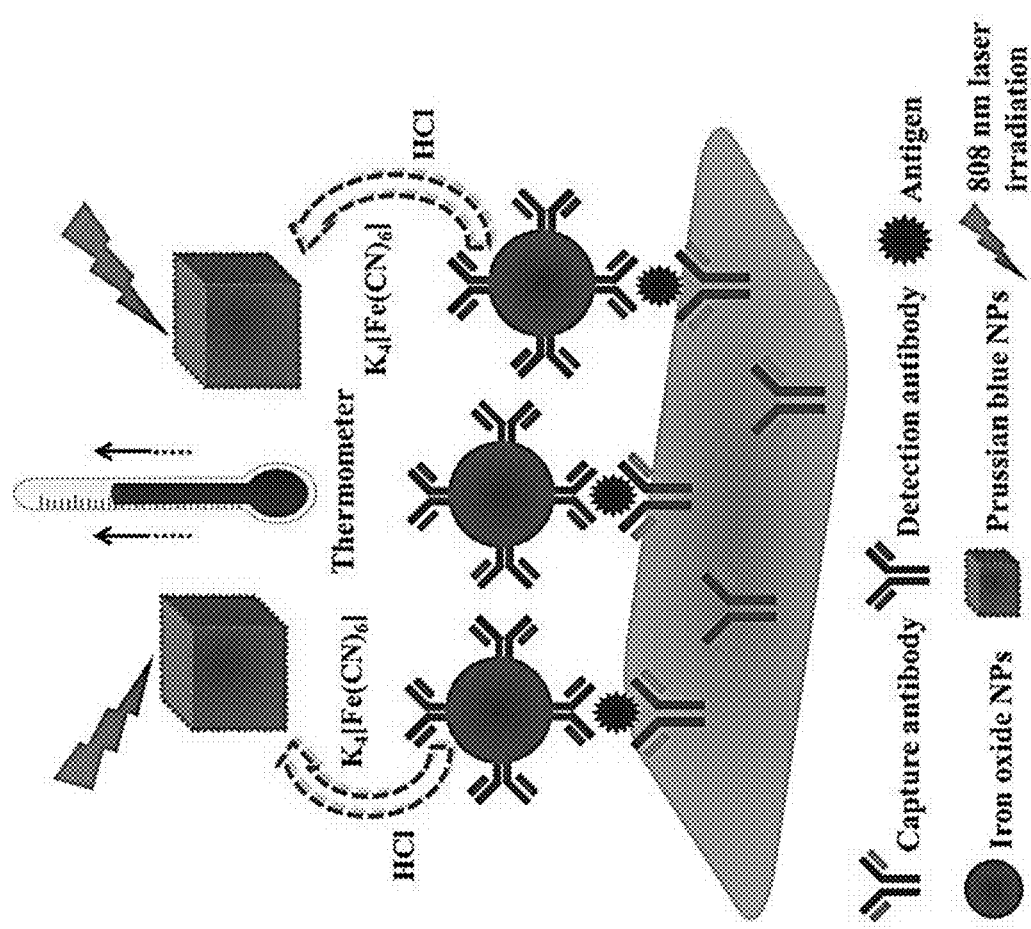
FIG. 2. Illustration of the photothermal immunoassay based on the Iron oxide-to-Prussian blue nanoparticle conversion strategy.

Without relying on advanced analytical equipment, the photothermal immunoassay can employ a common thermometer for sensitive quantitative readout based on thermogenic moieties attached to or generated by NPs (e.g., FIG. 1) or the photothermal conversion effect of NPs (e.g., FIG. 2). To demonstrate certain aspects of photothermal immunoassays prostate-specific antigen (PSA) was used as the model analyte. Iron oxide NPs captured in a sandwich immuno-detection system can be used as an oxidizing agent to produce or generate a photothermal moiety, such as the charge transfer complex of the one-electron oxidation product of TMB (oxidized TMB), or can be transformed into a highly photothermally effective Prussian blue NPs, which then act as the photothermal probe to convert the detection signal into heat through the photothermal conversion effect. The efficient photothermal conversion effect resulting from the iron-oxide oxidation of a thermogenic moiety or iron oxide-to-Prussian blue transformation process allows the sensitive quantitative readout of PSA using a thermometer. In addition, the process can also results in an obvious change in color, which could be used as a colorimetric probe for qualitative detection.

I. PHOTOTHERMAL IMMUNOASSAYS

Embodiments of the invention are directed to nanomaterial-based photothermal immunoassays employing a thermometer for sensitive quantitative readout of analyte levels based on a photothermal strategy. One photothermal strategy is using the oxidation of a precursor photothermal agent by an iron oxide particle to produce a photothermal agent (e.g., the oxidation of TMB) (for example see FIG. 1). Another photothermal strategy is using the highly photothermally effective Prussian blue NPs obtained from the Iron oxide-to-Prussian blue nanoparticle transformation process as the photothermal probe to convert the detection signal into thermometer-detectable heat though the photothermal conversion effect, thus allowing efficient quantitative readout of analyte levels using a thermometer (for an example see FIG. 2). The photothermal strategy has wide-ranging applications from clinical diagnostics to various chemistry and biochemistry analysis. Most importantly, the introduction of the photothermal strategy to realize the thermometer-based readout method provides opportunities for advances in clinical diagnostics and highly efficient POC diagnostics.

Analytes can be detected using the photothermal methodologies described herein in a variety of assays including, but not limited to immuno-detection, microchip, or lateral flow based methods. In certain aspects the analyte detection methods employ an analyte specific ELISA assay. In certain aspects, antibodies directly or indirectly coupled to a thermogenic nanoparticle (a nanoparticle that is coupled to, can be transformed into, or catalyzes the production of a photothermal agent) are used to detect the presence of an analyte in an original or processed sample. In certain aspects the sample is a biological sample obtained from a subject. Samples obtained from a subject may include, for example, cells, tissue, blood, serum, or urine. For example, a sample can be blood or urine collected from a subject. A sample can be analyzed directly or extracted/processed before analysis.

In certain aspects a sample is contacted with an effective amount of one or more binding agent that specifically binds the target analyte to form a complex. The complex or binding reaction is then detected directly when the binding reagent is coupled to a thermogenic agent or indirectly by contacting the complex with a second thermogenic agent that specifically binds the complex or the binding reagent, or the analyte present in the complex. In certain embodiments the binding reagent is an antibody or antibody fragment. The antibody can be coupled to a thermogenic agent, such as a NP as described herein.

In other embodiments, the analyte in the sample is immobilized on a surface and detected. In certain aspects analyte is immobilized prior to introduction of the thermogenic agent, and the amount of the signal, corresponding to the amount of thermogenic agent bound, correlates to the amount of analyte in the sample. In still other embodiments, the analyte is captured by an immobilized unlabeled first binding reagent, after which a thermogenic second agent is introduced to bind to the captured analyte and produce a signal in proportion to the amount of captured analyte.

A thermogenic agent can be coupled to a first antibody and used as a binding agent in a direct assay or coupled to a secondary antibody to detect a first preformed antibody/analyte complex in an indirect assay. Additionally, an antibody can be used in a competition assay to detect analytes in a sample. For example, analytes in a sample are captured by an unlabeled antibody immobilized on the surface of an ELISA well and then detected by a labeled (thermogenic) antibody of the same or different kind and/or specificity. Alternatively, the sample can be suspended in a buffer and mixed directly with an antibody, thus allowing the antibody to form an immune complex with the analyte. The reduction of free antibody due to complex formation can then be determined in a second step, based on solid-phase ELISA with purified analytes by comparing the relative reactivity of free residual antibody left over after sample incubation (sample reactivity) to that of the same antibody when not mixed with the sample (reference reactivity). The ratio of sample to reference antibody reactivity will be inversely proportional to the amount of analyte in the sample.

In certain aspects, methods of the invention can be adapted for lateral flow assays and other immunoassays and devices supporting such assays. Lateral flow assays, also known as immunochromatographic assays, are typically carried out using a simple device intended to detect the presence (or absence) of a target analyte in the sample. Most commonly these tests are used for medical diagnostics either for home testing, point of care testing, or laboratory use. Often produced in a dipstick format, these assays are a form of immunoassay in which the test sample flows along a solid substrate via capillary action. After the sample is applied to the test it encounters a colored or labeling reagent (thermogenic agent) which mixes with the sample and transits the substrate encountering lines or zones which have been pretreated with an antibody or antigen or affinity reagent. Depending upon the analyte present in the sample the colored or labeling reagent can become bound at the test line or zone. Lateral flow assays can operate as either competitive or sandwich assays.

As used herein, the term "carrier," such as used in a lateral flow assay, refers to any substrate capable of providing liquid flow. This would include, for example, substrates such as nitrocellulose, nitrocellulose blends with polyester or cellulose, untreated paper, porous paper, rayon, glass fiber, acrylonitrile copolymer, plastic, glass, or nylon. The substrate may be porous. Typically, the pores of the substrate are of sufficient size such that the nanoparticles of the invention flow through the entirety of the carrier. One skilled in the art will be aware of other materials that allow liquid flow. The carrier may comprise one or more substrates in fluid communication. For example, the reagent zone and detection zone may be present on the same substrate (i.e., pad) or may be present on separate substrates (i.e., pads) within the carrier.

As used herein, "porous membrane," such as used in a flow through assay, refers to a membrane or filter of any material that wets readily with an aqueous solution and has pores sufficient to allow nanoparticles of the invention to pass through. Suitable materials include, for example, nitrocellulose, nitrocellulose blends with polyester or cellulose, untreated paper, porous paper, rayon, glass fiber, acrylonitrile copolymer, plastic, glass, or nylon.

As used herein, "absorbing material" refers to a porous material having an absorbing capacity sufficient to absorb substantially all the liquids of the assay reagents and any wash solutions and, optionally, to initiate capillary action and draw the assay liquids through the test device. Suitable materials include, for example, nitrocellulose, nitrocellulose blends with polyester or cellulose, untreated paper, porous paper, rayon, glass fiber, acrylonitrile copolymer, plastic, glass, or nylon.

As used herein the term "lateral flow" refers to liquid flow along the plane of a carrier. In general, lateral flow devices may comprise a strip (or several strips in fluid communication) of material capable of transporting a solution by capillary action, i.e., a wicking or chromatographic action, wherein different areas or zones in the strip(s) contain assay reagents either diffusively or non-diffusively bound that produce a detectable signal as the solution is transported to or through such zones. Typically, such assays comprise an application zone adapted to receive a liquid sample, a reagent zone spaced laterally from and in fluid communication with the application zone, and a detection zone spaced laterally from and in fluid communication with the reagent zone. The reagent zone may comprise a compound that is mobile in the liquid and capable of interacting with an analyte in the sample and/or with a molecule bound in the detection zone. The detection zone may comprise a binding molecule that is immobilized on the strip and is capable of interacting with the analyte and/or the reagent compound to produce a detectable signal. Such assays may be used to detect an analyte in a sample through direct (sandwich assay) or competitive binding. Examples of lateral flow devices are provided in U.S. Pat. No. 6,194,220 to Malick et al.; U.S. Pat. No. 5,998,221 to Malick et al.; U.S. Pat. No. 5,798,273 to Shuler et al.; and U.S. Pat. No. RE38,430 to Rosenstein.

In a sandwich lateral flow assay, a liquid sample that may or may not contain an analyte of interest is applied to the application zone and allowed to pass into the reagent zone by capillary action. The analyte, if present, interacts with a labeled reagent in the reagent zone and the analyte-reagent complex moves by capillary action to the detection zone. The analyte-reagent complex becomes trapped in the detection zone by interacting with a binding molecule specific for the analyte and/or reagent. Unbound sample may move through the detection zone by capillary action to an absorbent pad laterally juxtaposed and in fluid communication with the detection zone. The labeled reagent may then be detected in the detection zone by appropriate means.

In a competitive lateral flow assay, a liquid sample that may or may not contain an analyte of interest is applied to the application zone and allowed to pass into the reagent zone by capillary action. The reagent zone comprises a labeled reagent, which may be the analyte itself, a homologue or derivative thereof, or a moiety that is capable of mimicking the analyte of interest when binding to an immobilized binder in the detection zone. The labeled reagent is mobile in the liquid phase and moves with the liquid sample to the detection zone by capillary action. The analyte contained in the liquid sample competes with the labeled reagent in binding to the immobilized binder in the detection zone. Unbound sample may move through the detection zone by capillary action to an absorbent pad laterally juxtaposed and in fluid communication with the detection zone. The labeled reagent may then be detected in the detection zone by appropriate means. The presence or absence of the analyte of interest may be determined through inspection of the detection zone, wherein the greater the amount of analyte present in the liquid sample, the lesser the amount of labeled receptor bound in the detection zone.

As used herein, the terms "vertical flow" and "flow through" refer to liquid flow transverse to the plane of a carrier. In general, flow through devices may comprise a membrane or layers of membranes stacked on top of each other that allow the passage of liquid through the device. The layers may contain assay reagents either diffusively or non-diffusively bound that produce a detectable signal as the solution is transported through the device. Typically, the device comprises first layer having an upper and lower surface, wherein said upper surface is adapted to receive a liquid sample, and an absorbent layer vertically juxtaposed and in fluid communication with the lower surface of the first layer that is adapted to draw the liquid sample through the first layer. The first layer may comprise a binding agent attached to the upper surface of the first layer that is capable of interacting with an analyte in the sample and trapping the analyte on the upper surface of the first layer. Examples of flow through devices are provided in U.S. Pat. No. 4,920,046 to McFarland et al. and U.S. Pat. No. 7,052,831 to Fletcher et al.

In practice, a liquid sample that may or may not contain an analyte of interest is applied to the upper surface of a first layer comprising a binding agent specific for an analyte of interest. The liquid sample then flows through the first layer and into the absorbent layer. If analyte is present in the sample, it interacts with the binding agent and is trapped on the upper surface of the first layer. The first layer may then be treated with wash solutions in accordance with conventional immunoassay procedures. The first layer may then be treated with a labeled reagent that binds to the analyte trapped by the binding agent. The labeled reagent then flows through the first layer and into the absorbent layer. The first layer may be treated with wash solutions in accordance with conventional immunoassay procedures. The labeled reagent may then be detected by appropriate means. Alternatively, the liquid sample may be mixed with the labeled reagent before being applied to the upper surface of the first layer. Other suitable variations are known to those skilled in the art.

Lateral and flow through assays may be used to detect multiple analytes in a sample. For example, in a lateral flow assay, the reagent zone may comprise multiple labeled reagents, each capable of binding to (or mimicking) a different analyte in a liquid sample, or a single labeled reagent capable of binding to (or mimicking) multiple analytes. Alternatively, or in addition, the detection zone in a lateral flow assay may comprise multiple binding molecules, each capable of binding to a different analyte in a liquid sample, or a single binding molecule capable of binding to multiple analytes. In a flow through assay, the porous membrane may comprise multiple binding agents, each capable of binding to a different analyte in a liquid sample, or a single binding agent capable of binding to multiple analytes. Alternatively, or in addition, a mixture of labeled reagents may be used in a flow through assay, each configured to bind to a different analyte in a liquid sample, or a single labeled reagent configured bind multiple analytes. If multiple labeled reagents are used in a lateral or flow through assay, the reagents may be differentially labeled to distinguish different types of analytes in a liquid sample.

As used herein, the term "mobile" means diffusively or non-diffusively attached, or impregnated. The reagents which are mobile are capable of dispersing with the liquid sample and are carried by the liquid sample in the lateral or vertical flow.

As used herein, the term "labeled reagent" means any particle, protein, or molecule which recognizes or binds to the analyte of interest and has attached to it a substance capable of producing a signal that is detectable visually or by thermometer, that is, a thermogenic nanomaterial as defined herein. The particle or molecule recognizing the analyte can be either natural or non-natural. In some embodiments the molecule is a monoclonal or polyclonal antibody.

As used herein, the term "binding reagent" means any particle or molecule which recognizes or binds a target analyte. The binding reagent is capable of forming a binding complex with the analyte-labeled reagent complex. The binding reagent can be immobilized to a carrier in the detection zone or to the surface of a membrane or support. The particle or molecule can be natural, or non-natural, e.g., synthetic.

As used herein, "detection zone" means the portion of the carrier or support containing an immobilized binding reagent.

The term "control zone" refers to a portion of the test device comprising a binding molecule configured to capture the labeled reagent. In a lateral flow assay, the control zone may be in liquid flow contact with the detection zone of the carrier, such that the labeled reagent is captured in the control zone as the liquid sample is transported out of the detection zone by capillary action. In a flow through assay, the control zone may be a separate portion of the porous membrane, such that the labeled reagent is applied both to the sample application portion of the porous membrane and the control zone. Detection of the labeled reagent in the control zone confirms that the assay is functioning for its intended purpose.

As used herein, "thermometer" refers to an instrument capable of measuring temperature or heat. In certain aspects a thermometer measures the temperature or temperature change caused the by presence of the thermogenic nanomaterial or photothermal agent. In certain aspects the thermometer is a pen digital thermometer, a thermocouple thermometer, a mercury-in-glass thermometer or other types of glass thermometers, an IR thermometer, and any other types of temperature sensors.

II. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Photothermal Immunoassay Employing TMB-H$_2$O$_2$ Colorimetric System

A. Materials And Methods

Materials and Instruments.

Carboxyl-functionalized iron oxide NPs with diameters of 30 nm were purchased from Ocean NanoTech LLC (USA). Polyclonal rabbit anti-human PSA antibody, monoclonal mouse anti-human PSA antibody and carcino-embryonic antigen (CEA) were purchased from Abcam (USA). Prostate specific antigen (PSA), bovine serum albumin (BSA), and serum from normal human male AB plasma were obtained from Sigma-Aldrich (USA). Hepatitis B surface antigen (HBsAg) was acquired from Fitzgerald Industries International Inc. (USA). 3,3',5,5'-tetramethylbenzidine (TMB) was purchased from Sigma-Aldrich (USA). Otherwise stated, all other chemicals were of analytical grade and used as received.

The diode laser with the wavelength of 808 nm and the output power intensity adjustable from 0 to 2.5 W was obtained from Opto Engine LLC (USA). The KT-300 LCD pen-style digital thermometer with the detection range from −50 to +300° C. was purchased from a local supermarket. Photographs were taken with a Canon EOS 600D camera. UV-Vis spectra was performed on a SPECTROstar Nano Microplate Reader (BMG LABTECH) using a 96-well microplate.

Preparation of Antibody-Conjugated Iron Oxide NPs.

Polyclonal rabbit anti-human PSA antibody was covalently conjugated to carboxyl-functionalized iron oxide NPs through the typical carbodiimide method according to the literature (Jaetao et al., 2009, Cancer Res. 69:8310-16). Typically, 1.0 mg iron oxide NPs were dispersed in 2.0 mL deionized water with ultrasonication. The aqueous mixture (25.0 µL) of N-hydroxysulfosuccinimide (Sulfo-NHS) and 1-ethyl-3-[3-dimethylaminopropyl]carbodiimide hydrochloride (EDC) with the same concentration of 25 mg·mL$^{-1}$ was added to the iron oxide NPs dispersion, followed by reaction at room temperature for 30 min under gentle stirring. 80.0 µg polyclonal rabbit anti-human PSA antibody was then added into the above nanoparticle dispersion, followed by reaction at room temperature for 2.0 h under gentle stirring. The nanoparticle dispersion was centrifuged at 11000 rpm for 10 minutes at 4.0° C. to collect the antibody-conjugated iron oxide NPs, which were then thoroughly washed with PBS (pH=7.4, 0.01 M) for 3 times. The antibody-conjugated iron oxide NPs were finally dispersed in 2.0 mL PBS (pH=7.4, 0.01 M) containing 0.2% BSA. The nanoparticle dispersions were stored at 4.0° C. before use.

Sandwich-Type Immunoassay.

A 120 µL monoclonal mouse anti-human PSA antibody solution (30 µg·mL$^{-1}$) was added in each polymerase chain reaction (PCR) tube (200 µL), which was then incubated for 12 h at 4.0° C. 200 µL blocking buffer containing 5.0% BSA was used to block each PCR tube, followed by incubation with 120 µL normal human (3-fold diluted with PBS) containing different concentrations of standard PSA for 2.0 h at 37.5° C. After thorough washing, a 120 µL polyclonal anti-PSA antibody-conjugated iron oxide NPs suspension (0.5 mg·mL$^{-1}$) was added into each tube for further incubation at 37.5° C. for 2.0 h. Finally, the PCR tubes were thoroughly washed with PBS for the following $Fe_3O_4$ NPs-mediated TMB-$H_2O_2$ colorimetric reaction.

To perform the colorimetric reaction, a 150 µL phosphate-citrate buffer (0.2 M, pH=5.0) containing TMB (0.4 mM) and $H_2O_2$ (1.0 M) was added in each PCR tube, followed by incubation at room temperature for 40 min. The solutions were thoroughly mixed every 5 min during the incubation. After incubation for 40 min, the colorimetric reaction solutions were used for photograph collection, UV-Vis spectroscopic characterization and photothermal detection.

Photothermal Detection and Immunoassay.

To monitor the photothermal effect of $Fe_3O_4$ NPs-mediated TMB-$H_2O_2$ colorimetric reaction solutions, different concentrations of $Fe_3O_4$ NPs were dispersed in 0.15 mL phosphate-citrate buffer solutions (0.2 M, pH=5.0) containing TMB (0.4 mM) and $H_2O_2$ (1.0 M). After incubation for 40 min, the reaction solutions were irradiated vertically with the 808 nm laser for different times (10-60 s) at a power density of 5.26 W·cm$^{-2}$. The temperature of the solutions was measured immediately after the irradiation using a pen-style digital thermometer. To monitor the photothermal process of the $Fe_3O_4$ NPs-mediated TMB-$H_2O_2$ colorimetric reaction solution, the colorimetric reaction solution (1.0 mL, 0.006 mg·mL$^{-1}$ $Fe_3O_4$ NPs) was irradiated horizontally with the laser for 10 min at a power density of 3.12 W·cm$^{-2}$. The pen-style digital thermometer was inserted into the solution to monitor the temperature during the irradiation. To monitor the photothermal effect of the $Fe_3O_4$ NPs-mediated TMB-$H_2O_2$ colorimetric immunoassay solutions, the immunoassay solutions (0.15 mL) obtained from different concentrations of PSA (1.0-64.0 ng·mL$^{-1}$) were irradiated vertically with the laser for 20 s at a power density of 5.26 W·cm$^{-2}$. It should be noted that the laser power density changed (3.12 or 5.26 W·cm$^{-2}$) due to different laser irradiation directions and different surface areas over varying situations. For example, either a PCR tube or a glass cuvette was used to study different aspects of the method, one being qualitatively and another being quantitatively.

Specificity of the Photothermal Immunoassay.

To study the specificity of the photothermal immunoassay, some common interfering substances including carcinoembryonic antigen (CEA), immunoglobulin G (IgG), hepatitis B surface antigen (HBsAg) and bovine serum albumin (BSA) were tested with the photothermal and colorimetric immunoassay. Human serum samples (3-fold diluted with PBS) spiked with CEA (320 ng·mL$^{-1}$), IgG (320 ng·mL$^{-1}$), HBsAg (320 ng·mL$^{-1}$), BSA (320 ng·mL$^{-1}$) and PSA (32.0 ng·mL$^{-1}$) were tested with the colorimetric, UV-Vis spectroscopic and photothermal immunoassay, respectively.

B. Results

Investigation of Photothermal Effect of the TMB System.

Iron oxide NPs have been well established as efficient artificial horseradish peroxidase (HRP) to catalyze the oxidation of TMB in the presence of $H_2O_2$. (Yu et al., Biomaterials 2009, 30, 4716-22; Woo et al., Int. J. Mol. Sci. 2013, 14, 9999-10014). Based on the color change from the oxidation product of TMB, the $Fe_3O_4$ NPs-mediated TMB-$H_2O_2$ colorimetric system has been widely used for immunoassay (Woo et al., Int. J. Mol. Sci. 2013, 14, 9999-10014). Along with the color change, it is worth noting that significant changes in optical absorption properties often occur, providing the possibilities for photothermal conversion.

Figures 3A, 3B, 3C:
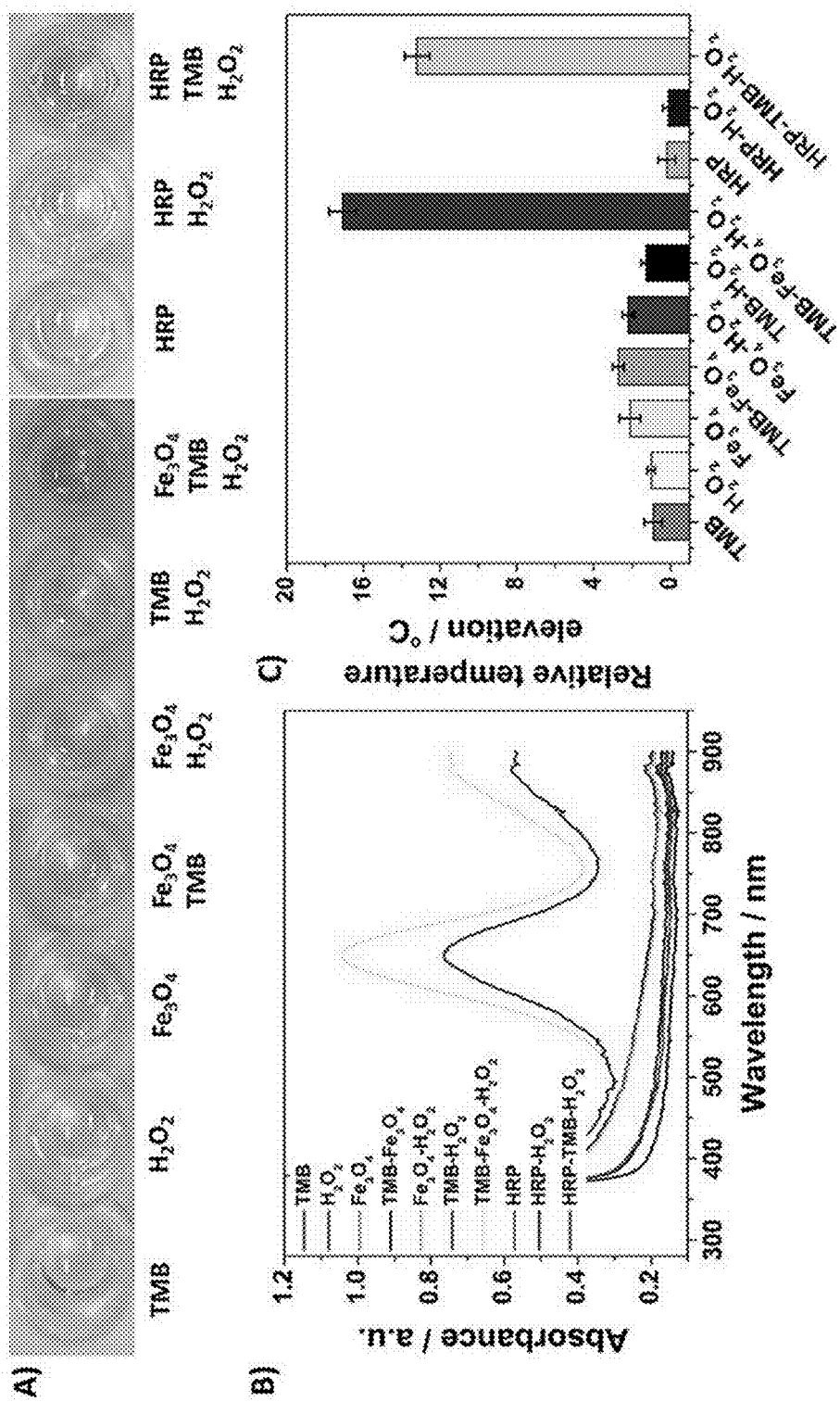
FIG. 3A-3C. (3A) Photographs of the $Fe_3O_4$ NPs-catalyzed TMB-$H_2O_2$ colorimetric reaction solutions with different components. (3B) UV-vis spectra of the colorimetric reaction solutions with different components. (3C) Temperature change of the colorimetric reaction solutions (0.15 mL) with different components after the 808 nm laser irradiation for 20 s. The final concentrations of $Fe_3O_4$ NPs, HRP, TMB and $H_2O_2$ in the colorimetric reaction solutions are 0.006 mg·mL$^{-1}$, 0.002 U·mL$^{-1}$, 0.4 mM and 1.0 M, respectively. Error bars indicate standard deviations (n=4).

To study the possibilities of the $Fe_3O_4$ NPs-mediated TMB-$H_2O_2$ colorimetric system for photothermal conversion, the colorimetric, optical and photothermal properties of the system were systematically studied. FIG. 3 shows the photographs, UV-Vis spectra and 808 nm laser-driven photothermal effect of the colorimetric reaction systems with different components. Significantly, only in the co-presence of $Fe_3O_4$ NPs, TMB and $H_2O_2$, a rapid color change from colorless to blue was observed, whereas no apparent color changes were exhibited in other cases without the co-presence of $Fe_3O_4$ NPs, TMB and $H_2O_2$ (FIG. 3A). The result indicated the successful $Fe_3O_4$ NPs-mediated TMB-$H_2O_2$ colorimetric reaction, where $Fe_3O_4$ NPs catalyzed the oxidation of TMB to its oxidized form (oxidized TMB) with blue color. To further confirm the colorimetric reaction, the traditional HRP-catalyzed TMB-$H_2O_2$ colorimetric system was carried out. Similarly, the typical blue color was observed only in the co-presence of HRP, TMB and $H_2O_2$, further confirming the successful $Fe_3O_4$ NPs (artificial HRP)-mediated TMB-$H_2O_2$ colorimetric reaction.

As expected, only with the appearance of the blue color in both $Fe_3O_4$ NPs- and HRP-mediated TMB-$H_2O_2$ reaction systems, strong characteristic absorption peaks were observed at 650 nm in UV-Vis spectra (FIG. 3B). The absorption peak derives from the oxidation product of TMB (oxidized TMB) during the colorimetric reactions (Gao et al., *Sci. Rep.* 2014, 4, 3966; Woo et al., *Int. J. Mol. Sci.* 2013, 14, 9999-10014). It is worth noting that the absorbance of oxidized TMB increased drastically at 750 nm in the NIR region, whereas no apparent light absorption was observed when no color changes were observed. The significant light absorption of oxidized TMB in the NIR region provides the possibilities for NIR laser-driven photothermal conversion.

To test the photothermal effect of the colorimetric reaction system, different components from the reaction system were exposed to an 808 nm laser at a power density of 5.26 W·cm$^{-2}$ for 20 s. A pen-style digital thermometer was employed to measure the temperature immediately after the irradiation. Dramatic temperature increase was observed only with the appearance of the blue color after the irradiation. Surprisingly high temperature increases of 17.9 and 13.2° C. were recorded from the $Fe_3O_4$ NPs- and HRP-mediated TMB-$H_2O_2$ reaction solutions (FIG. 3C), respectively, while no significant temperature increases were found in other cases without color changes. These results demonstrated remarkable NIR laser-driven photothermal effect of the $Fe_3O_4$ NPs/HRP-mediated TMB-$H_2O_2$ colorimetric systems, which originated from the oxidation product of TMB (oxidized TMB) due to its strong light absorption in the NIR region. Similar to some other nanomaterial-based photothermal agents (Chen et al., *Biomaterials* 2014, 35, 8206-8214), the colorimetric product, oxidized TMB, can act as the photothermal probe to convert the adsorbed NIR light into heat, since the adsorbed light is not released in fluorescence or other forms of energy. The NIR laser-driven photothermal effect of some small organic molecules had been reported for photothermal therapy of cancers (Shan et al., *Theranostics* 2013, 3, 267-74; Wu et al., *Biomacromolecules* 2013, 14, 3027-33; Cheng et al., *Adv. Funct. Mater.* 2013, 23, 5893-902).

Figures 4A, 4B, 4C:
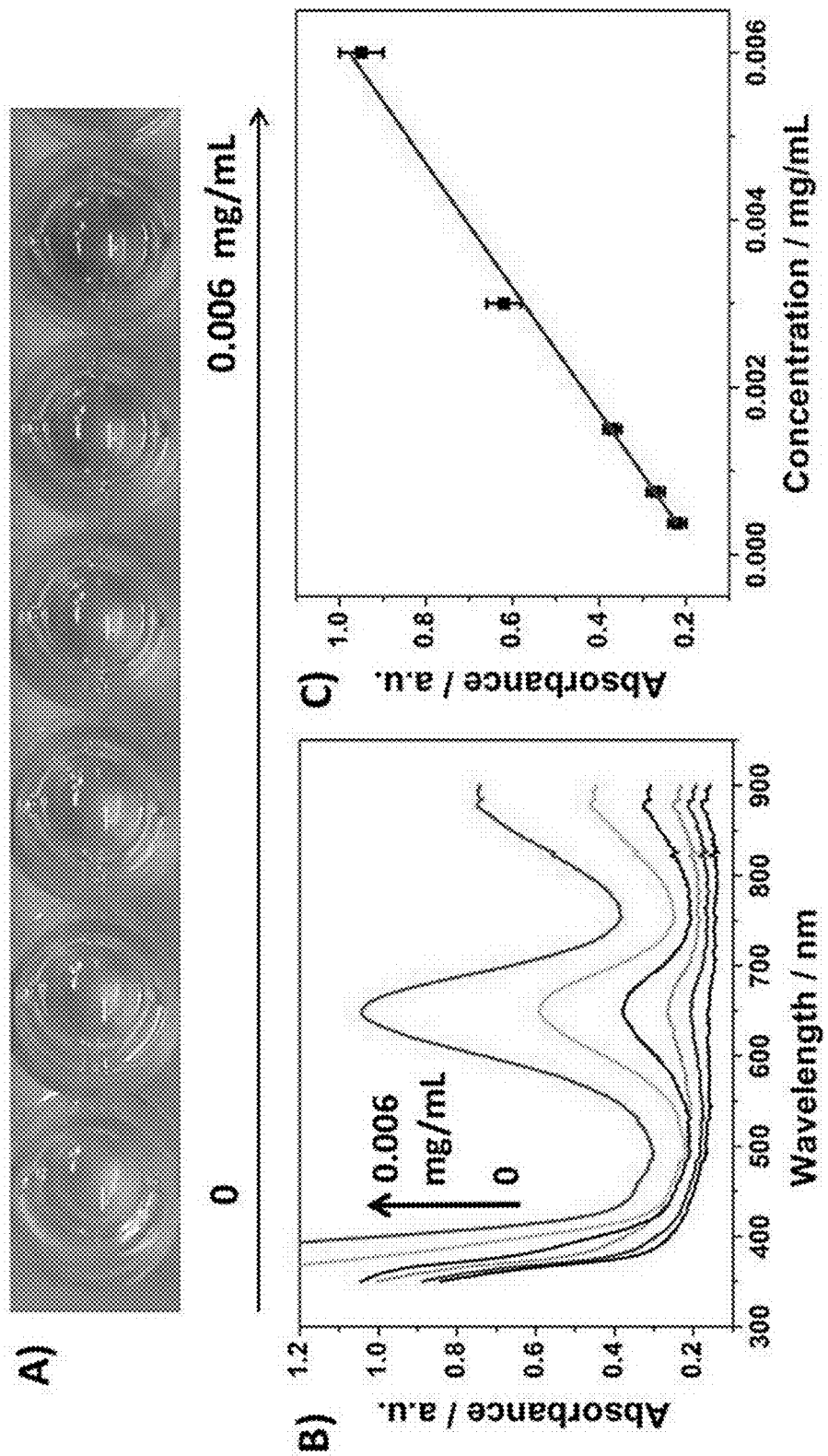
FIG. 4A-4C. (4A) Photographs of the TMB-$H_2O_2$ colorimetric reaction solutions catalyzed by different concentrations of $Fe_3O_4$ NPs in the range from 0 to 0.006 mg·mL$^{-1}$. (4B) UV-vis spectra of the colorimetric reaction solutions catalyzed by different concentrations of $Fe_3O_4$ NPs. (4C) Calibration plot of absorbance at 650 nm in UV-vis spectra of the colorimetric reaction solutions vs. concentration of $Fe_3O_4$ NPs.

To investigate the relationship between $Fe_3O_4$ NPs and oxidized TMB concentrations, the colorimetric reaction systems mediated by different concentrations of $Fe_3O_4$ NPs were then carried out. The reaction solutions showed a gradually darkening tendency from colorless to blue as the $Fe_3O_4$ NPs concentration increased in the range from 0.000375 to 0.006 mg·mL$^{-1}$ (FIG. 4A). In addition, the absorbance of oxidized TMB at 650 nm as well as the NIR region in UV-Vis spectra also increased accordingly (FIG. 4B). As the $Fe_3O_4$ NPs concentration increased, their peroxidase mimic activity improved, thus leading to the production of increasing concentration of oxidized TMB. It was found that the absorbance at 650 nm is proportional to the concentration of $Fe_3O_4$ NPs in the range from 0.000375 to 0.006 mg·mL$^{-1}$ with the square of the correlation coefficient of 0.99 (FIG. 4C). This linear relationship laid a base to link immunoassay information from $Fe_3O_4$ NPs to the photothermal effect of oxidized TMB.

Figures 5A, 5B:
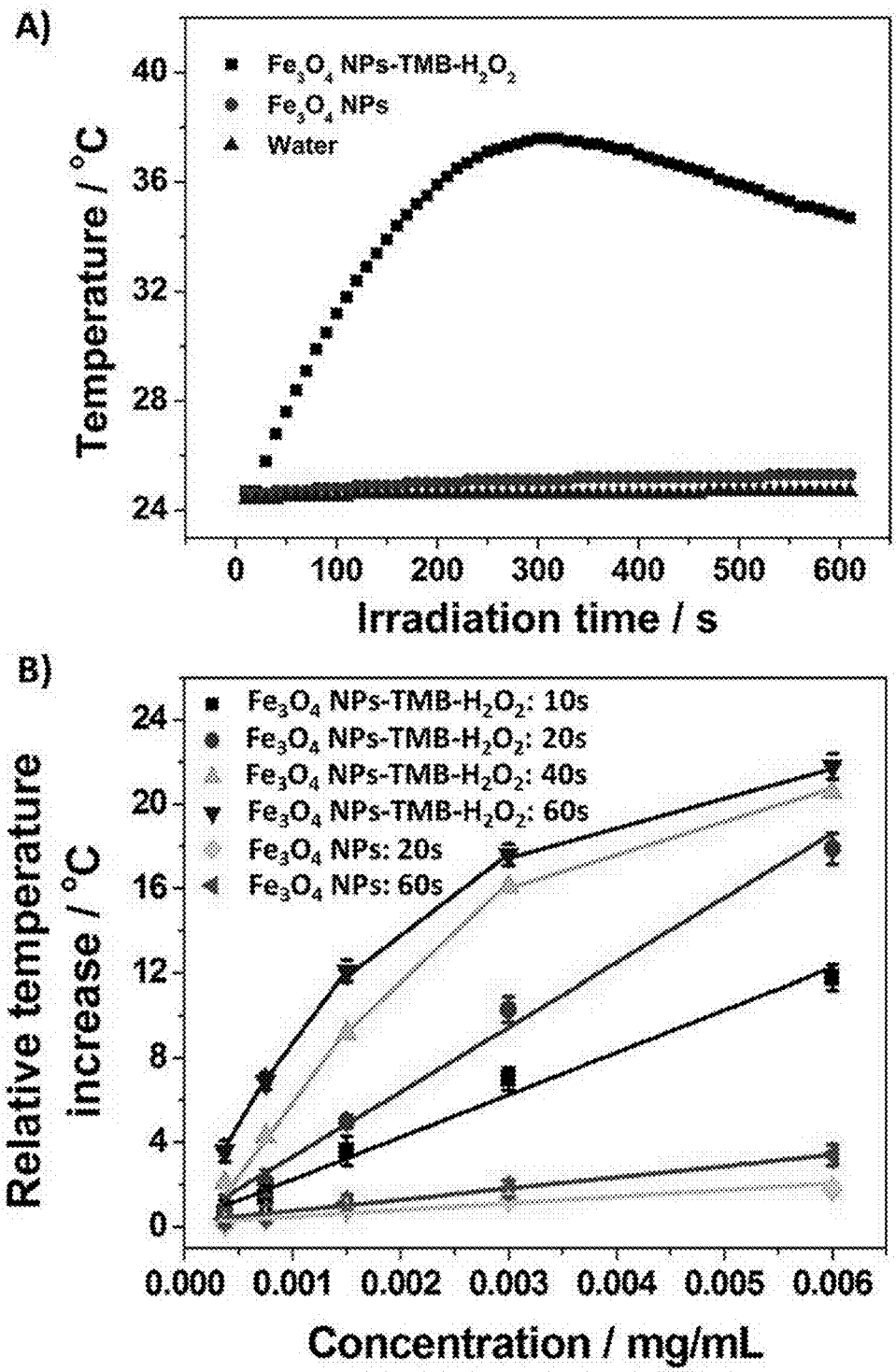
FIG. 5A-5B. (5A) Temperature of the $Fe_3O_4$ NPs (0.006 mg·mL$^{-1}$)-catalyzed TMB-$H_2O_2$ colorimetric reaction solution, $Fe_3O_4$ NPs aqueous dispersion and water during the irradiation of an 808 nm laser for 10 min at a power density of 3.12 W·cm$^{-2}$. (5B) Analytical relationship between the concentration of $Fe_3O_4$ NPs and the temperature elevation of the colorimetric reaction solutions as well as $Fe_3O_4$ NPs dispersions after irradiation at a power density of 5.26 W·cm$^{-2}$ for different time (10-60 s).

To study the feasibility of the photothermal strategy for thermometer-based analytical readout, the photothermal effect of the reaction systems mediated by different concentrations of $Fe_3O_4$ NPs were investigated. The colorimetric reaction solutions were irradiated for different times to monitor the temperature increase as shown in (FIG. 5B). As the $Fe_3O_4$ NPs concentration increased, the temperature increase from the solutions increased dramatically at various irradiation times from 10 to 60 s. The result can be attributed to the increasing concentration of the photothermal probe (oxidized TMB) in the solutions. In addition, the temperature elevation rate increased obviously as the irradiation time increased. The temperature increase at shorter irradiation time (10-20 s) was proportional to the concentration of $Fe_3O_4$ NPs in the range from 0.000375 to 0.006 mg·mL$^{-1}$ with slopes of 2003.8° C.·(mg·mL$^{-1}$)$^{-1}$ at 10 s and 3058.1° C.·(mg·mL$^{-1}$)$^{-1}$ at 20 s, respectively. The result was in good agreement with the linear relationship discussed in respect to FIG. 4C, indicating the feasibility of the thermometer-based readout method for monitoring the photothermal effect. However, a linear relationship was no longer observed at longer irradiation time (40-60 s), which might be attributed to photobleaching of oxidized TMB during longer-time irradiation. 20 s was thus used as the irradiation time in the following immunoassays to avoid photobleaching of the photothermal probe. $Fe_3O_4$ NPs showed minor temperature increases at both 20 and 60 s, confirming strong photothermal effect of oxidized TMB.

To further investigate the photobleaching of oxidized TMB during long-time irradiation, a $Fe_3O_4$ NPs-mediated TMB-$H_2O_2$ reaction solution was irradiated by the laser for 10 min to monitor its photothermal process. A pen-style thermometer was inserted into the solution to measure the temperature during the irradiation. The temperature of the solution increased rapidly from the initial temperature (24.5° C.) to 38.0° C. within the first 300 s, while no apparent temperature increase was observed in the blank, as shown in FIG. 5A. For comparison, the same concentration of $Fe_3O_4$ NPs dispersion was also irradiated, which exhibited a minor temperature increase of 1.0° C. These results further indicated the strong NIR laser-driven photothermal effect of oxidized TMB produced in the reaction solution. However, the temperature started to decrease after the plateau at around 320 s, indicating the time-dependent decrease in photothermal effect of oxidized TMB during the following irradiation process. The phenomenon is different from most photothermal nanomaterials, such as Prussian blue-, Gold- and Carbon-based nanomaterials (Fu et al. *Bioconjugate Chem.* 2014, 25: 1655-63; Fu et al., *Chem. Commun.* 2012, 48:11567-69; Ke et al., *Angew. Chem. Int. Edit.* 2011, 50:3017-21; Moon et al., *ACS Nano* 2009, 3:3707-13), which usually show constantly increasing temperature during the irradiation time of 10 min. Similar time-dependent decrease in the photothermal effect was also reported in the case of Indocyanine Green (IGG) due to the photobleaching of the organic molecule under NIR laser irradiation (Spence et al., *Chem. Sci.* 2013, 4:4240-44; Zheng et al., *ACS Nano* 2013, 7:2056-67; Bahmani et al., *Sci. Rep.* 2013, 3:2180). Compared with nanomaterials, the photothermal process of small organic molecules is more transient under high intensity irradiation, which could reach the saturated state rapidly within a short irradiation time. As a result, the photothermal effect could not be constantly achieved during long-time irradiation (Spence et al., *Chem. Sci.* 2013, 4:4240-44), thereby leading to the decrease of temperature.

Quantification of Disease Biomarkers in Human Serum Using the Thermometer-Based Photothermal Immunoassay.

Figures 6A, 6B, 6C:
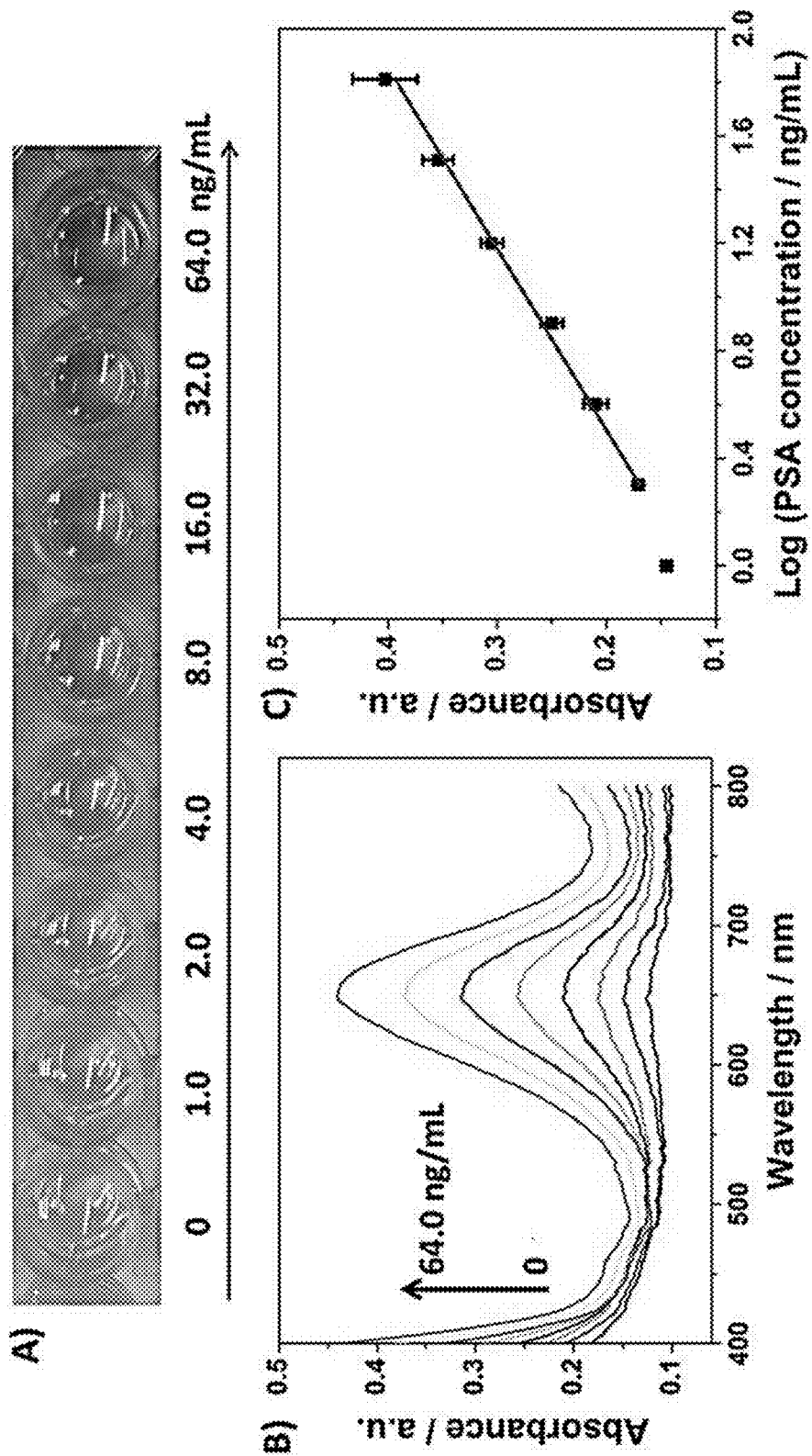
FIG. 6A-6C. (6A) Photographs of the $Fe_3O_4$ NPs-catalyzed TMB-$H_2O_2$ colorimetric immunodetection solutions obtained from different concentrations of (Prostate specific antigen) PSA in the range from 0 to 64.0 ng·mL$^{-1}$ (6B) UV-vis spectra of the colorimetric immunodetection solutions obtained from different concentrations of PSA. (C) Calibration plot of absorbance at 650 nm in UV-vis spectra of the colorimetric immunodetection solutions vs. logarithm of PSA concentration in the range from 2.0 to 64.0 ng·mL$^{-1}$.

On the basis of the above studies of the photothermal effect of oxidized TMB, the photothermal effect of the $Fe_3O_4$ NPs-mediated TMB-$H_2O_2$ immunoassay system was then explored using prostate specific antigen (PSA) as the model analyte. Normal human serum spiked with different concentrations of standard PSA were used for this investigation. As PSA concentration increased in the range from 1.0 to 64.0 ng·mL$^{-1}$, the immunoassay solutions exhibited a gradually darkening tendency from colorless to blue as shown in FIG. 6. The result indicated the increasing concentration of the photothermal probe (oxidized TMB) in the immunoassay solutions as PSA concentration increased. In addition, the absorbance of oxidized TMB at 650 nm as well as the NIR region increased obviously as PSA concentration increased (FIG. 6B). The absorbance at 650 nm was proportional to logarithm of PSA concentration in the range from 2.0 to 64.0 ng·mL$^{-1}$ with the square of the correlation coefficient of 0.99 (FIG. 6C). Although the color changes from FIG. 6A can be used for qualitative or semi-quantitative analysis, a UV-Vis spectrometer is usually required to accurately quantify the concentrations of PSA in serum samples.

Figure 7:
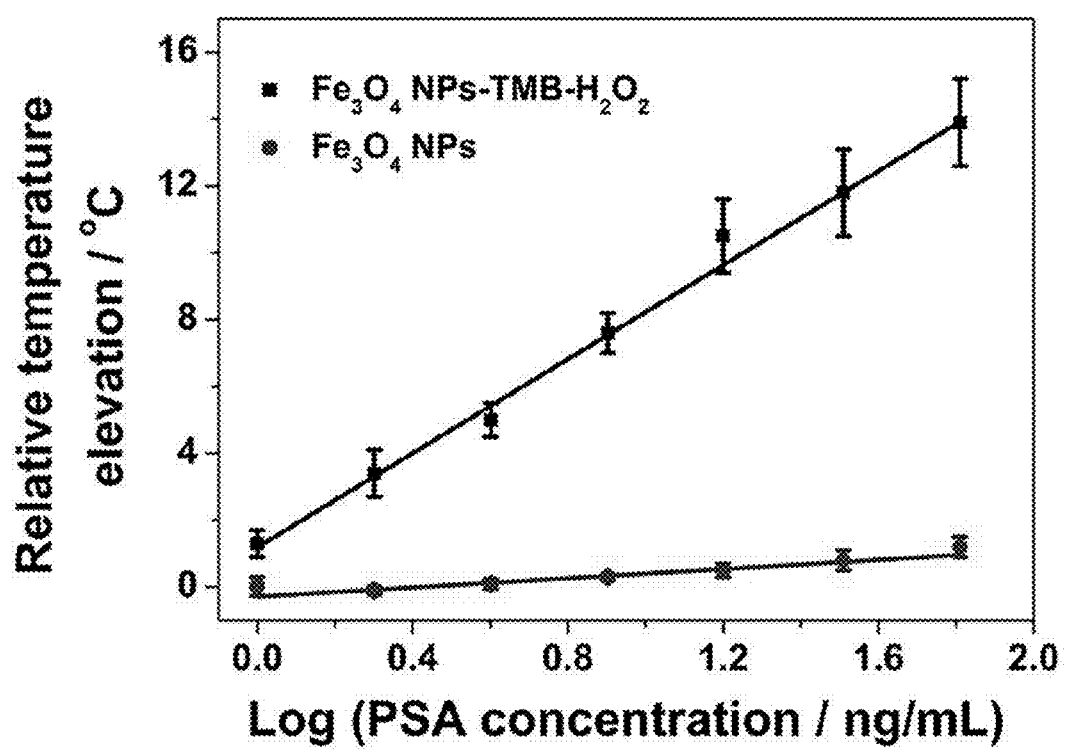
FIG. 7. Calibration plots of relative temperature elevation of the immunodetection solutions with ($Fe_3O_4$ NPs-TMB-$H_2O_2$) and without ($Fe_3O_4$ NPs) the colorimetric reaction after irradiation at a power density of 5.26 W·cm$^{-2}$ for 20 s vs. logarithm of PSA concentration.

To evaluate the feasibility of the photothermal strategy for thermometer-based quantitative immunoassay, the immunoassay solutions were irradiated with the laser for 20 s to investigate their photothermal effect. Excitingly, the temperature elevation increased dramatically with the increase of PSA concentrations after the irradiation (FIG. 7), which can be attributed to the production of increasing concentrations of the photothermal probe (oxidized TMB) in the immunoassay solutions. Significantly, a high temperature increase of 13.5° C. was monitored at the PSA concentration of 64.0 ng·mL$^{-1}$, while an obvious temperature increase of 1.4° C. was observed even at 1.0 ng·mL$^{-1}$. In contrast, only minor temperature increases were observed at various PSA concentrations in the absence of TMB and $H_2O_2$ in the immunoassay system. These results demonstrated that the photothermal strategy can convert the immunoassay signal into heat, thereby allowing sensitive readout of PSA concentrations using a thermometer. Hence, a new photothermal immunoassay strategy becomes feasible using only a common thermometer as the quantitative signal reader.

It was found that the temperature increase was proportional to the logarithm of PSA concentration in the range from 1.0 to 64.0 ng·mL$^{-1}$ with the square of the correlation coefficient of 0.99 (Y(° C.)=7.03·Log $C_{PSA}$(ng·mL$^{-1}$)+1.19). By using only a common thermometer for quantitative readout, PSA can be determined at a concentration as low as 1.0 ng·mL$^{-1}$ in normal human serum. Although this concentration is relatively higher than that of some traditional methods such as the electrochemical and fluorescent methods (Chen et al., *Anal. Chem.* 2014, 86:7337-42; Choi et al., *Biosens. Bioelectron.* 2013, 49:415-19; Liu et al., *Chem. Commun.* 2013, 49:6602-04), it is comparable to the conventional ELISA method (LOD: 1.0 ng·mL$^{-1}$) and commercialized PSA ELISA kit (LOD: 1.0 ng·mL$^{-1}$, Biocell Biotechnol. Co., Ltd., Zhengzhou, China) using spectrometers as previously reported in the literature (Gao et al., *Sci. Rep.* 2014, 4:3966). Furthermore, it is worth noting that the developed photothermal immunoassay can completely meet the requirement of clinical prostate cancer diagnostics, because the threshold concentration of total PSA concentration in human serum for prostate cancer diagnosis is 4.0 ng·mL$^{-1}$ (Gao et al., *Sci. Rep.* 2014, 4:3966; Lee et al., *Sci. Rep.* 2014, 4:7352). Herein, 808 nm was used as the irradiation wavelength because it has been widely used as the model wavelength for investigation of NIR laser-driven photothermal effect (Fu et al., *Chem. Commun.* 2012, 48:11567-69; Ke et al., *Angew. Chem. Int. Edit.* 2011, 50:3017-21). However, it should be noted that the photothermal detection sensitivity can be further improved at other irradiation wavelengths, such as the absorption peak at 650 nm and 900 nm in the NIR region, due to the increasing absorbance of the photothermal probe at these wavelengths.

Specificity and Reproducibility of the Thermometer-Based Photothermal Immunoassay.

Figures 8A, 8B, 8C:
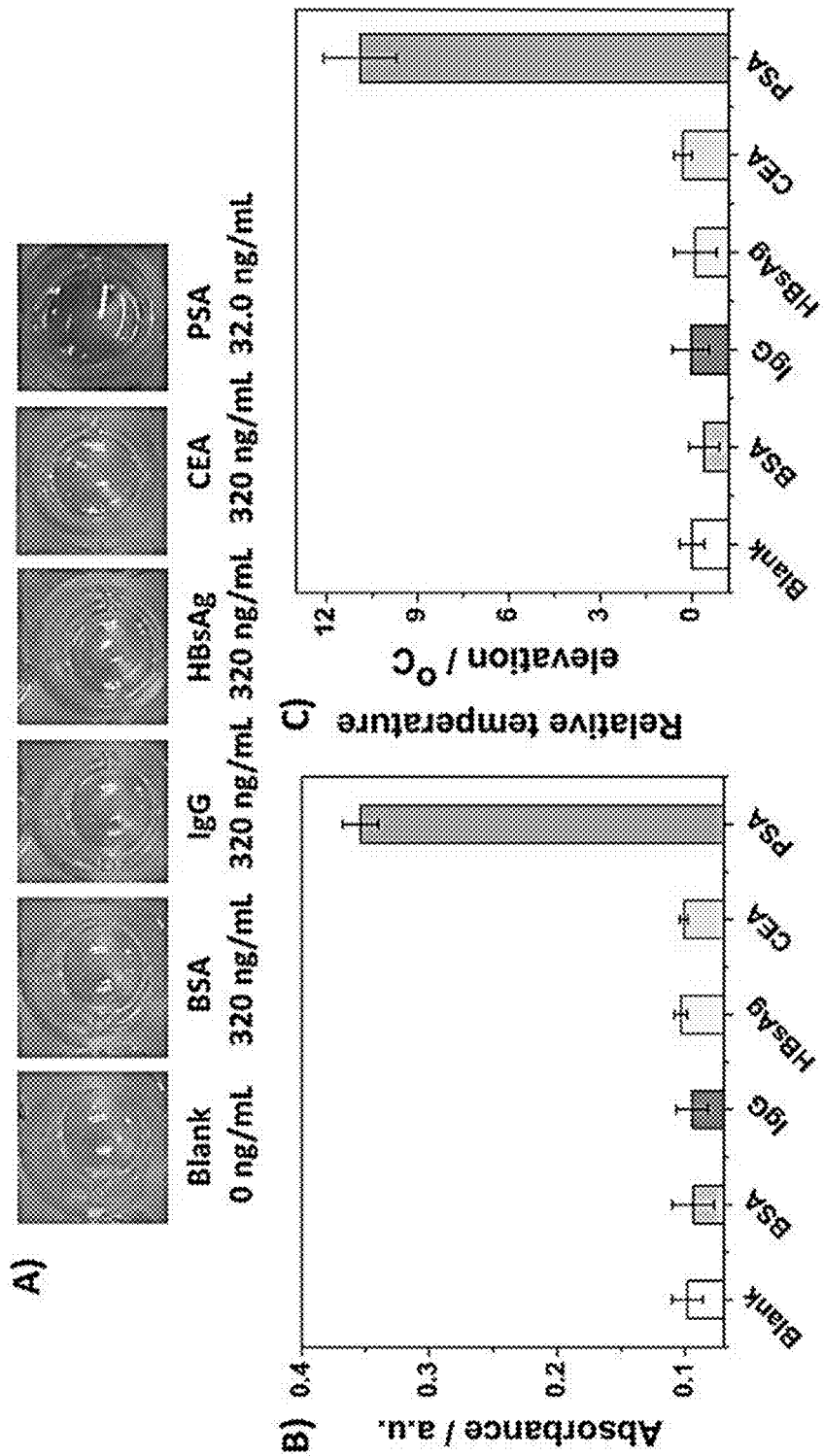
FIG. 8A-8C. (8A) Photographs of the $Fe_3O_4$ NPs-catalyzed TMB-$H_2O_2$ colorimetric immunodetection solutions obtained from PSA and different interfering substances. (8B) Absorbance at 650 nm in UV-vis spectra of the colorimetric immunodetection solutions obtained from PSA (32.0 ng·mL$^{-1}$) and different interfering substances (320 ng·mL$^{-1}$). (8C) Temperature elevation of the colorimetric immunodetection solutions obtained from PSA (32.0 ng·mL$^{-1}$) and different interfering substances (320 ng·mL$^{-1}$) after irradiation at a power density of 5.26 W·cm$^{-2}$ for 20 s.

To study the specificity of the photothermal immunoassay for determination of target PSA, some common interfering substances including carcino-embryonic antigen (CEA), immunoglobulin G (IgG), hepatitis B surface antigen (HBsAg) and bovine serum albumin (BSA) were tested using both the colorimetric and photothermal immunoassay. A dramatic temperature increase of 10.9° C. was monitored for target PSA (32.0 ng·mL$^{-1}$), while no significant temperature change was observed for the interfering substances with 10-fold higher concentrations as shown in FIG. 8. Additionally, significant color change and characteristic absorption peak of oxidized TMB at 650 nm in UV-Vis spectra were observed only for target PSA. These results demonstrated high specificity of the photothermal and colorimetric immunoassay for determination of target PSA in the presence of high concentrations of interfering substances.

To study the reproducibility of the photothermal immunoassay, the temperature increase of six immunoassay solutions at the same PSA concentration was tested. The RSD of the temperature increase from these six immunoassay solutions was 5.12%. Furthermore, five immunoassay solutions were tested at different times over a period of five weeks (once a week). The RSD of temperature increase was 6.20% over the time period of five weeks. These results demonstrated acceptable reproducibility of the photothermal immunoassay.

Example 2

Photothermal and Colorimetric Immunoassy Using Transformation of Iron Oxide Nanoparticles to Prussion Blue Nanoparticles A. Materials and Methods Carboxyl-functionalized iron oxide nanoparticles (NPs) with a diameter of 40 nm were purchased from Ocean NanoTech LLC (USA). Polyclonal rabbit anti-human PSA antibody, monoclonal mouse anti-human PSA antibody and carcino-embryonic antigen (CEA) were purchased from Abcam (USA). Prostate-specific antigen (PSA), bovine serum albumin (BSA) and serum from normal human male AB plasma were obtained from Sigma-Aldrich (USA). Hepatitis B surface antigen (HBsAg) was acquired from Fitzgerald Industries International Inc. (USA). PB NPs were typically prepared according to the published literature (Fu et al., *Chem. Commun.*, 2012, 48:11567-69). Unless otherwise stated, all other chemicals were of analytical grade and used as received.

The diode laser with the wavelength of 808 nm and the output power intensity adjustable from 0 to 2.5 W was obtained from Opto Engine LLC (USA). The KT-300 LCD pen-style digital thermometer with the detection range from −50 to +300° C. was purchased from a local supermarket. Photographs were taken with a Canon EOS 600D camera.

Preparation of Antibody-Conjugated Iron Oxide NPs.

The polyclonal rabbit anti-human PSA antibody was covalently conjugated to carboxyl-functionalized iron oxide NPs through the typical carbodiimide method. Typically, 1.0 mg iron oxide NPs were dispersed in 2.0 mL deionized water with ultrasonication. The aqueous mixture (25.0 µL) of N-hydroxysulfosuccinimide (Sulfo-NHS) and 1-ethyl-3-[3-dimethylaminopropyl]carbodiimide hydrochloride (EDC) with the same concentration of 25.0 mg·mL$^{-1}$ was added to the nanoparticle dispersion, followed by reactions at room temperature for 30 min under gentle stirring. 80.0 µg polyclonal rabbit anti-human PSA antibody was then added into the above nanoparticle dispersion, followed by reactions at room temperature for 2.0 h under gentle stirring. The nanoparticle dispersion was centrifuged at 11,000 rpm for 10.0 minutes at 4.0° C. to collect the antibody-conjugated iron oxide NPs, which were then washed with PBS (pH=7.4, 0.01 M) for 3 times. The antibody-conjugated iron oxide NPs were finally dispersed in 2.0 mL PBS (pH=7.4, 0.01 M) containing 0.2% BSA. The nanoparticle dispersions were stored at 4.0° C. before use.

Procedures of the Colorimetric Immunoassay.

A 100 µL monoclonal mouse anti-human PSA antibody solution (30.0 µg·mL$^{-1}$) was added in each PCR tube (200 µL) and incubated for 12.0 h at 4.0° C. A 200 µL blocking buffer containing 5.0% BSA was then used to block the tubes for 2.0 h at 37.5° C., followed by incubation with different concentrations of standard PSA solutions containing 5.0% BSA for 2.0 h at 37.5° C. After thoroughly washing, a 100 µL polyclonal anti-PSA antibody-conjugated iron oxide NPs suspension (0.5 mg·mL$^{-1}$) was added in each tube for further incubation at 37.5° C. for 2.0 h. Finally, the PCR tubes were thoroughly washed with PBS.

To transform iron oxide NPs captured in the sandwich-type immunosensing system into PB NPs, a 120 µL HCl solution (0.1 M) was added into each tube, followed by ultrasonication for 1.0 h at room temperature. A 30.0 µL potassium ferrocyanide aqueous solution (90.0 mM) was then added into each tube to produce PB NPs from the reaction between ferric ions and ferrocyanide ions under acidic condition. The immunosensing solutions were thoroughly mixed every 10 min, and were finally used for the UV-Vis spectroscopic characterization, Fourier transform infrared spectroscopic (FTIR) and Transmission electron microscopic (TEM) characterization after the reaction for 1.0 h.

Characterization and Instruments.

UV-Vis spectrometry, FTIR and TEM were used to characterize the immunosensing solutions before and after the iron oxide-to-PB NPs conversion process. UV-Vis spectra of the immunosensing solutions were performed on a 96-well microplate using a SPECTROstar Nano Microplate Reader (BMG LABTECH). FTIR was performed on a Spectrum 100 FT-IR spectrometer (PerkinElmer, Inc.). Immunosensing solutions at the PSA concentration of 64.0 ng·mL$^{-1}$ before and after the iron oxide-to-PB NPs conversion process were dropped on Whatman® cellulose chromatography papers (Sigma-Aldrich), followed by air dry at room temperature for the FTIR measurement using the chromatography paper as the blank. TEM was carried out to observe the morphology of nanoparticles in the immunosensing solutions using a JOEL 3200FS cryo-Transmission electron microscope Immunosensing solutions at the PSA concentration of 64.0 ng·mL$^{-1}$ before and after the iron oxide-to-PB NPs conversion process were deposited on carbon-coated copper grids for the TEM imaging. Additionally, photographs were taken with a Canon EOS 600D camera to record the color changes.

Colorimetric Detection in Human Serum.

Serum from normal humans was used for the real sample detection to validate the reliability of the developed colorimetric immunoassay. 10.0 µL different concentrations of standard PSA solutions were spiked into 1.0 mL human serum which was pre-diluted 3 folds with PBS to prepare the spiked serum samples with the final PSA concentrations of 4.0, 8.0 and 16.0 ng·mL$^{-1}$, respectively. After thoroughly mixing, the concentrations of PSA in the spiked serum samples were tested with the developed colorimetric immunoassay. In addition, to validate the analytical reliability of the developed colorimetric immunoassay for detection of real human serum samples, the conventional UV-Vis spectrometry was used to measure the PSA spiked in the human serum samples to calculate the spike recoveries.

Photothermal Detection Protocol.

For monitoring of temperature elevation of iron oxide NPs and PB NPs during the irradiation process for 10 min, 1.0 mL of the nanoparticle dispersions in disposable UV cuvettes were irradiated with a 808 nm laser at a power density of 3.12 W·cm$^{-2}$ for 10 min. A pen-type digital thermometer without exposure to the laser was inserted into the nanoparticle dispersions to monitor the temperature. The temperature was recorded every 10 seconds during the irradiation process for 10 min.

For photothermal immunoassay, the PCR tubes containing 0.15 mL immunoassay solutions were exposed to a 808 nm laser at a power density of 5.26 W·cm$^{-2}$ for 1.5 min. After the irradiation, a pen-style digital thermometer was immediately inserted into the solutions to monitor the temperature.

Photothermal Detection in Human Serum Samples.

Serum samples from normal human were used to validate the reliability of the developed photothermal immunoassay. 10 µL different concentrations of standard PSA solutions were spiked into 1.0 mL 3-fold diluted human serum to prepare the real serum samples with final PSA concentrations of 4.0, 8.0 and 16.0 ng·mL$^{-1}$, respectively. After thoroughly mixing, the concentrations of PSA in the spiked serum samples were tested with the developed photothermal immunoassay to evaluate the recoveries of PSA spiked in the serum samples using unspiked human serum as the blank.

B. Results

Characterization and Confirmation of the Nanoparticle Colorimetric Conversion Process.

Figures 9A, 9B, 9C:
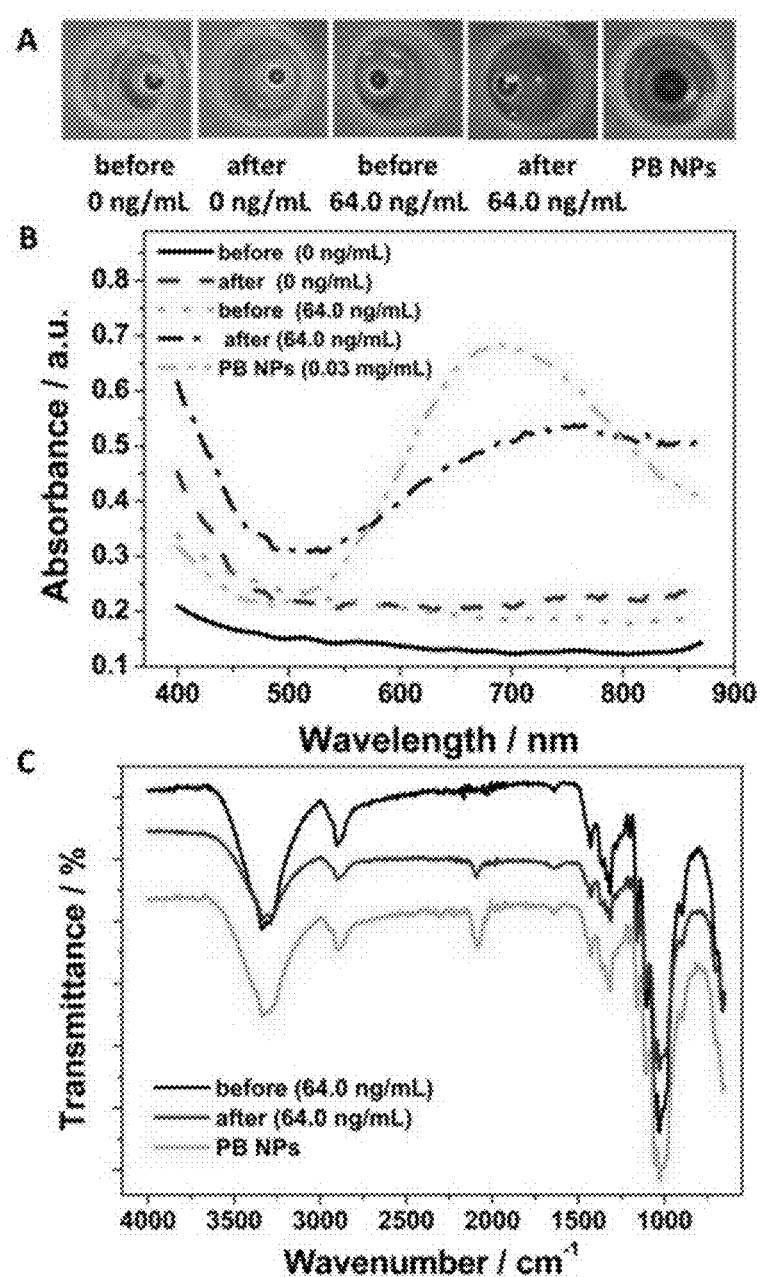
FIG. 9A-9C. Photographs (9A) and UV-Vis spectra (9B) of PB NPs aqueous dispersion and the immunosensing solutions at different PSA concentrations before and after the nanoparticle conversion process. (9C) FTIR of PB NPs and the immunosensing solution at the PSA concentration of 64.0 ng·mL$^{-1}$ before and after the nanoparticle conversion process. The reaction time of the nanoparticle conversion process was 1.0 h.

To confirm the generation of PB NPs in the immunosensing solutions after the iron oxide-to-PB NPs conversion process, colorimetric, UV-Vis spectroscopic and Fourier transform infrared spectroscopic (FTIR) characterization were carried out. FIG. 9A shows the photographs of the immunosensing solutions before and after the nanoparticle conversion process. No apparent color change was observed in the absence of the target PSA after the nanoparticle conversion process, indicating the absence of PB NPs in the immunosensing solution, because no iron oxide NPs were captured in the immunosensing system without the target PSA. As expected, a clear color change from light brown to bright blue was observed in the presence of 64.0 ng·mL$^{-1}$ PSA after the nanoparticle conversion process. The light brown color before the nanoparticle conversion process was attributed to the iron oxide NPs captured in the immunosensing system. The bright blue color after the nanoparticle conversion process was consistent with the typical color of PB NPs, revealing the generation of PB NPs in the immunosensing solution.

With the clear color change after the nanoparticle conversion process, a broad absorption peak was observed at 748 nm in the UV-Vis spectra of the immunosensing solution (64.0 ng·mL$^{-1}$ PSA) (FIG. 2B), while no absorption peak was exhibited before the nanoparticle conversion process. The absorption peak corresponded well with that of PB NPs attributed to the charge transfer transition between Fe (II) and Fe (III) in PB NPs (Fu et al., Chem. Commun., 2012, 48:11567-69; Fu et al., Bioconjugate Chem., 2014, 25:1655-1663), demonstrating the generation of PB in the immunosensing solution after the nanoparticle conversion process. The slight redshift of the absorption peak of PB in the immunosensing solution might be attributed to the different matrix effect from the immunosensing solution. No noticeable absorption peak was recorded both before and after the nanoparticle conversion process in the absence of the target PSA, which indicated that no PB was generated in the absence of the target PSA. These results confirmed the successful iron oxide-to-PB conversion process in the presence of the target PSA, providing the possibilities for colorimetric immunosensing of PSA.

Along with color changes and UV-Vis spectra, FTIR was utilized to confirm the generation of PB in the immunosensing solution, as shown in FIG. 9C. As can be seen, an apparent stretching band was observed at 2085 cm$^{-1}$ after the nanoparticle conversion process, while no band was observed before the nanoparticle conversion process. Significantly, the stretching band corresponded well with that of PB NPs (2085 cm$^{-1}$), demonstrating the successful iron oxide-to-PB conversion process in the presence of the target PSA. The stretching band can be attributed to the CN stretching in the formed [Fe$^{II}$—CN—Fe$^{III}$] structure in PB NPs (Zhang et al., *J. Mater. Chem.*, 2010, 20:5110-16; Shokouhimehr et al., *Inorg. Chem. Commun.*, 2010, 13:58-61).

Figures 10A, 10B:
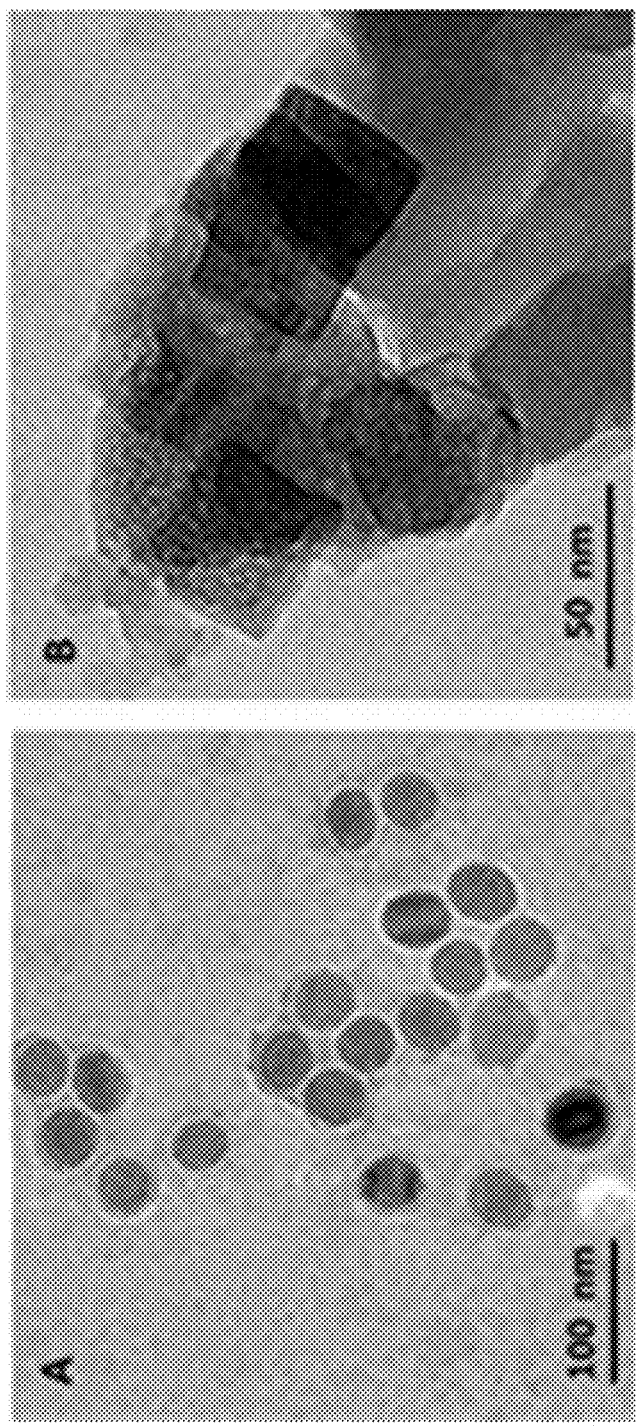
FIG. 10A-10B. TEM images of nanoparticles in immunosensing solutions at the PSA concentration of 64.0 ng·mL$^{-1}$ before (10A) and after (10B) the nanoparticle conversion process.

To further confirm the iron oxide-to-PB NPs conversion process, TEM was used to study the morphological change of nanoparticles in the immunosensing solutions. FIG. 10 shows the TEM images of nanoparticles in the immunosensing solutions before and after the nanoparticle conversion process. It can be seen that before the conversion, a number of iron oxide NPs with uniformly spherical morphology at an average diameter of 40 nm were observed in the TEM image, which was in good agreement with the product information from the manufacturer (Ocean NanoTech LLC, USA). However, an obvious change in morphology of the nanoparticles was observed after the nanoparticle conversion process. With the disappearance of the spherical iron oxide NPs, nanoparticles with clear cubic morphology at the size from 20 to 100 nm were observed in the TEM image. The cubic morphology of the nanoparticles was in good agreement with the well-known cubic morphology of PB NPs (Fu et al., *Chem. Commun.*, 2012, 48:11567-69; Hu et al., *Angew. Chem. Int. Edit.*, 2012, 51:984-88; Shokouhimehr et al., *J. Mater. Chem.*, 2010, 20:5251-59). Spherical iron oxide NPs captured in the sandwich-type immunoassay system were first dissolved in acidic conditions under ultrasonication to release ferric ions (Fe$^{3+}$), followed by the reaction between ferric ions and the added ferrocyanide ions to produce PB NPs that had a typical cubic morphology. The wide size distribution of PB NPs in the immunosensing solution can be due to the absence of surface capping agents during the nucleation between ferric ions and potassium ferrocyanide (Shokouhimehr et al., *J. Mater. Chem.*, 2010, 20:5251-59). These results further confirmed the successful spherical iron oxide-to-cubic PB NPs conversion process.

Colorimetric Immunosensing Using the Nanoparticle Conversion Strategy.

To study the feasibility of the iron oxide-to-PB NPs conversion strategy for colorimetric immunosensing, different concentrations of standard PSA in bovine serum albumin (BSA) solutions were tested with the immunoassay method illustrated in FIG. 2.

Figures 11A, 11B, 11C:
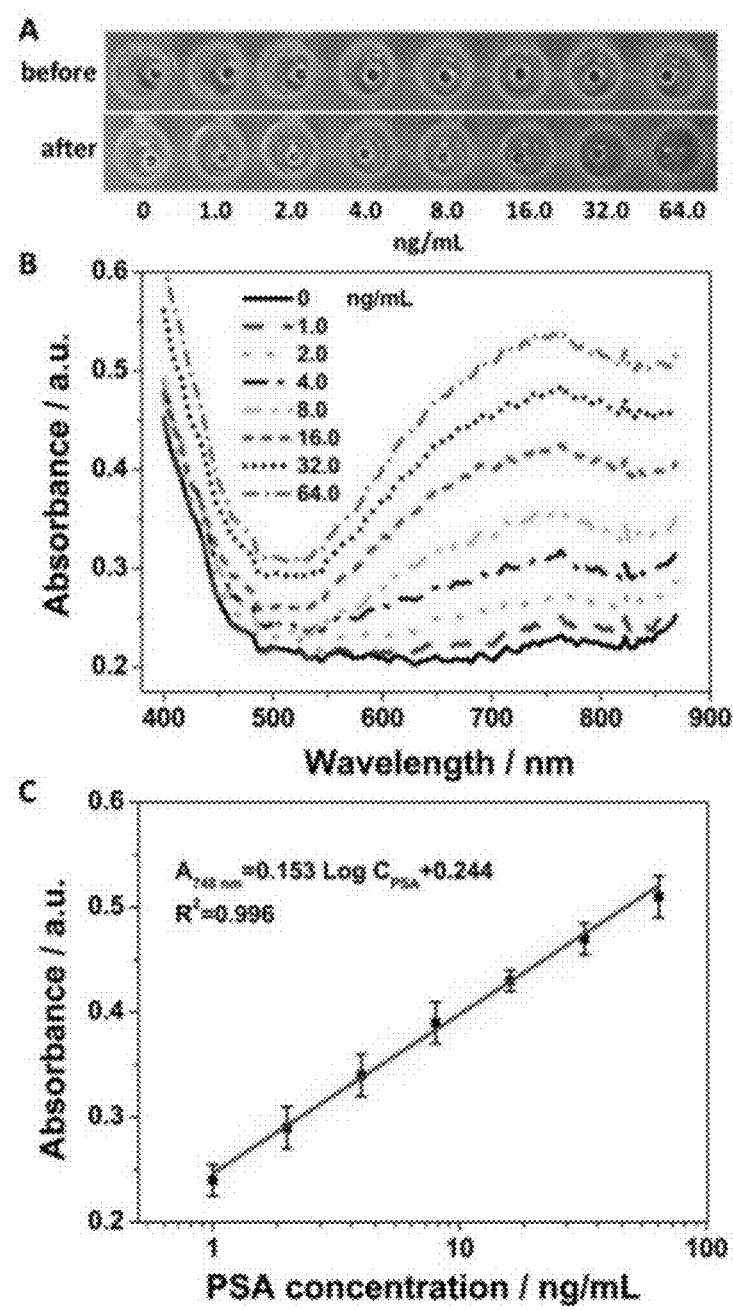
FIG. 11A-11C. Photographs (11A) and UV-Vis spectra (11B) of the immunosensing solutions at different PSA concentrations (5% BSA) before and after the nanoparticle conversion process. (11C) Calibration plot of absorbance at 748 nm in UV-Vis spectra vs. logarithm of the PSA concentration. Error bars indicate standard deviations (n=3).

FIG. 11A shows that as the PSA concentration increased in the range from 1.0 to 64.0 ng·mL$^{-1}$, a gradually deepening tendency from light yellow to bright blue in the color of the immunosensing solutions was observed after the nanoparticle conversion process. As the PSA concentration increased, the amount of iron oxide NPs captured in the immunosensing system increased accordingly, thereby resulting in the concentration increase of PB NPs generated from the iron oxide-to-PB NPs conversion process. It was reported that PB NPs showed high molar extinction coefficients comparable to that of gold nanorods in the near-infrared region (700-900 nm) (Fu et al., *Chem. Commun.*, 2012, 48, 11567-69). Therefore, by employing PB NPs with high structural stability and simple transformation as a colorimetric probe, the iron oxide-to-PB NPs conversion process provides a new promising strategy for cost-effective and easy-to-use colorimetric immunosensing. In addition, with the clear color change as the PSA concentration increased, the absorption peak of PB NPs at 748 nm in the UV-Vis spectra also increased (FIG. 11B). Excitingly, it was found that the absorbance at 748 nm was proportional to the logarithm of the PSA concentration in the range from 1.0 to 64.0 ng·mL$^{-1}$, the common clinically relevant diagnostic level (Barbosa et al., *Lab Chip*, 2014, 14, 2918-2928), with a correlation coefficient of 0.996 (FIG. 11C). The result demonstrated good correspondence between the colorimetric immunosensing and the UV-Vis spectrometry.

It was also found that visible color difference between 1.0 ng·mL$^{-1}$ PSA and the control can be distinguished by the naked eye, as shown in FIG. 11A, suggesting high sensitivity of the colorimetric immunosensing method without the aid of any nanoparticle stabilizing ligands and signal amplification process. The distinguishable color difference between 1.0 ng·mL$^{-1}$ PSA and the control was further confirmed by the UV-Vis spectra as shown in FIG. 11B. Hence, PSA could be quickly detected at a concentration as low as 1.0 ng·mL$^{-1}$ with the naked eye. Although this concentration is higher than that of some electrochemical and fluorescence methods (Chen et al., *Anal. Chem.*, 2014, 86:7337-42; Liu et al., Chen, *Chem. Commun.*, 2013, 49:6602-04), it is much lower (~80 folds) than that of the reported Au NPs-based colorimetric PSA assay (80 ng·mL$^{-1}$) (Drew, *Honors Theses*, 2015, Paper 113), indicating the high-sensitivity of our method. This LOD is also comparable to the conventional ELISA method (LOD: 1.0 ng·mL$^{-1}$) and commercial PSA ELISA kits (LOD: 1.0 ng·mL$^{-1}$, Biocell Biotechnol. Co., Ltd., Zhengzhou, China) using spectrometers as reported in the published literature (Gao et al., *Sci. Rep.*, 2014, 4:3966). Furthermore, it was worth noting that the colorimetric immunoassay can meet the requirement of clinical diagnostics because the threshold concentration of PSA in human serum in prostate cancer diagnostics is 4.0 ng·mL$^{-1}$ (Gao et al., *Sci. Rep.*, 2014, 4:3966).

Specificity of the Colorimetric Immunosensing Strategy.

Figures 12A, 12B:
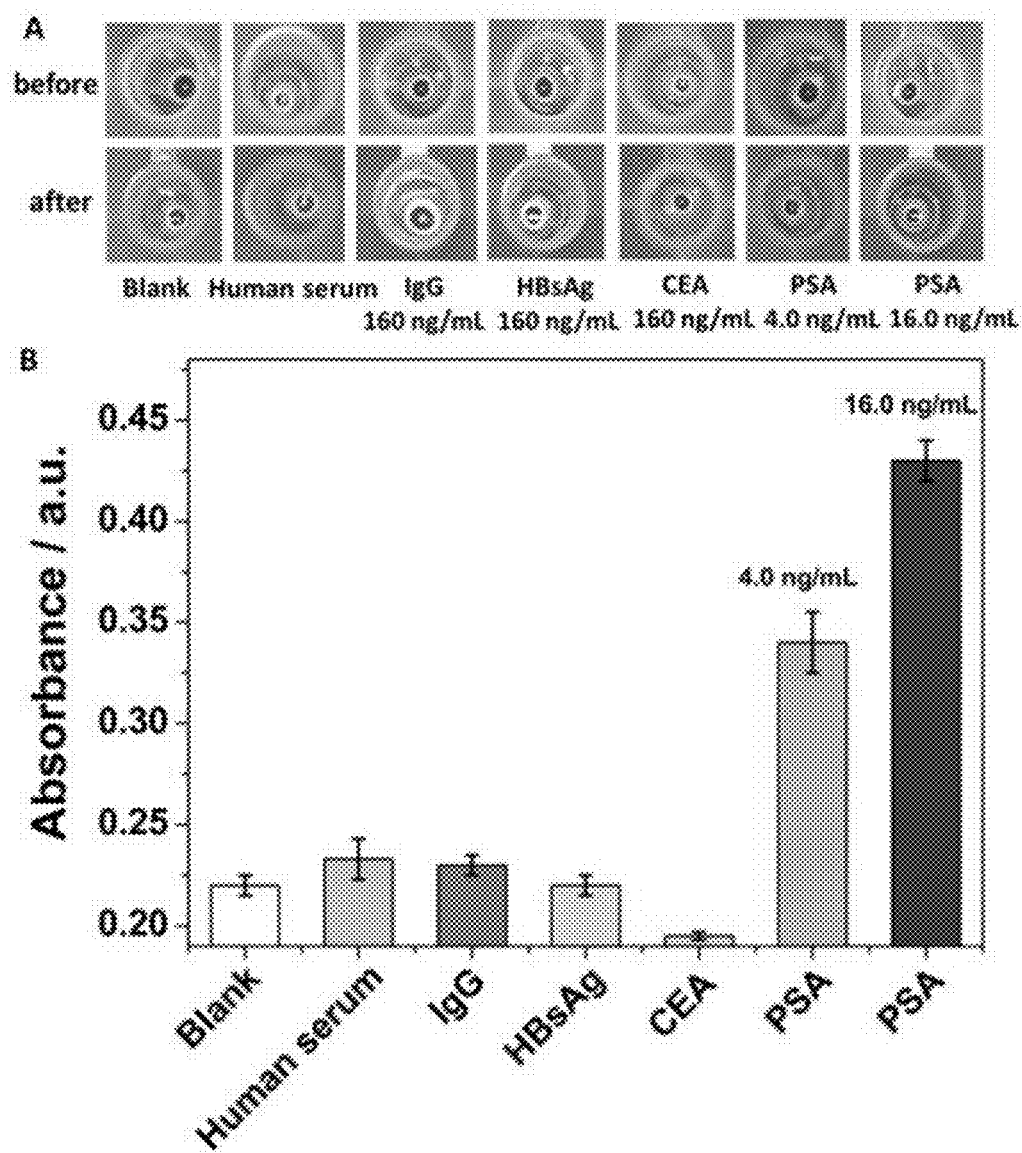
FIG. 12A-12B. Specificity study. Photographs (12A) and absorbance at 748 nm (12B) of the immunosensing solutions obtained from the target PSA and different interfering substances before and after the nanoparticle conversion process. Serum from normal human was pre-diluted 3 folds with PBS. Error bars indicate standard deviations (n=3).

To evaluate the specificity of the colorimetric immunosensing strategy, some other common interfering substances in serum with 10-fold higher concentrations than PSA (16.0 ng·mL$^{-1}$) including carcino-embryonic antigen (CEA), IgG, and hepatitis B surface antigen (HBsAg) were tested with the colorimetric immunoassay. It should be noted that 4.0 ng·mL$^{-1}$ was used as the lowest PSA concentration for specificity study because of its clinical diagnostic significance as a lower threshold diagnostic concentration (Gao et al., *Sci. Rep.*, 2014, 4:3966). Normal human serum was also used as an interfering substance. As shown in FIG. 12A, only the immunosensing solution obtained from the target PSA (4.0 and 16.0 ng·mL$^{-1}$) exhibited a clear color change to blue after the nanoparticle conversion process. In addition, the UV-Vis spectra (FIG. 12B) shows that only the immunosensing solution obtained from the target PSA had obvious absorption at 748 nm, while other interfering substances exhibited less than 4.7% absorbance in comparison with PSA (relative to blank). These results confirmed high anti-interference capability of the colorimetric immunosensing strategy for PSA detection in the presence of high concentrations of interfering substances.

Colorimetric Immunosensing in Human Serum Samples.

To validate the analytical accuracy of the developed colorimetric immunosensing method for detection of real samples, serum samples from normal human were spiked with different concentrations of standard PSA for the colorimetric determination. As an important lower threshold concentration for clinical prostate cancer diagnostics, 4.0 ng·mL$^{-1}$ was herein selected as the lowest spiked concentration for the validation study.

Figure 13:
FIG. 13. Detection of PSA spiked in human serum samples by the colorimetric immunoassay (n=4).
Figure 13:
Figure 13:
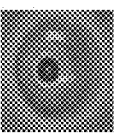
Figure 13:
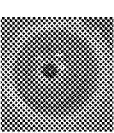

A distinct difference in the color of the immunosensing solutions was observed by the naked eye as shown in FIG. 13. As the concentration of PSA spiked in the serum increased, a deepening trend of the color to blue was exhibited, which was consistent with that from FIG. 11A. Additionally, in order to confirm the results from color changes, conventional UV-Vis spectrometry was further used to detect PSA in the spiked human serum samples. The detection results obtained from the UV-Vis spectroscopic measurement corresponded well with that of the color changes. The analytical recoveries were in the range from 91.3-93.1%, which were within the acceptable criteria for bioanalytical method validation (Zhou et al., *Angew. Chem. Int. Edit.*, 2014, 53:12498-502).

Figures 14, 15:
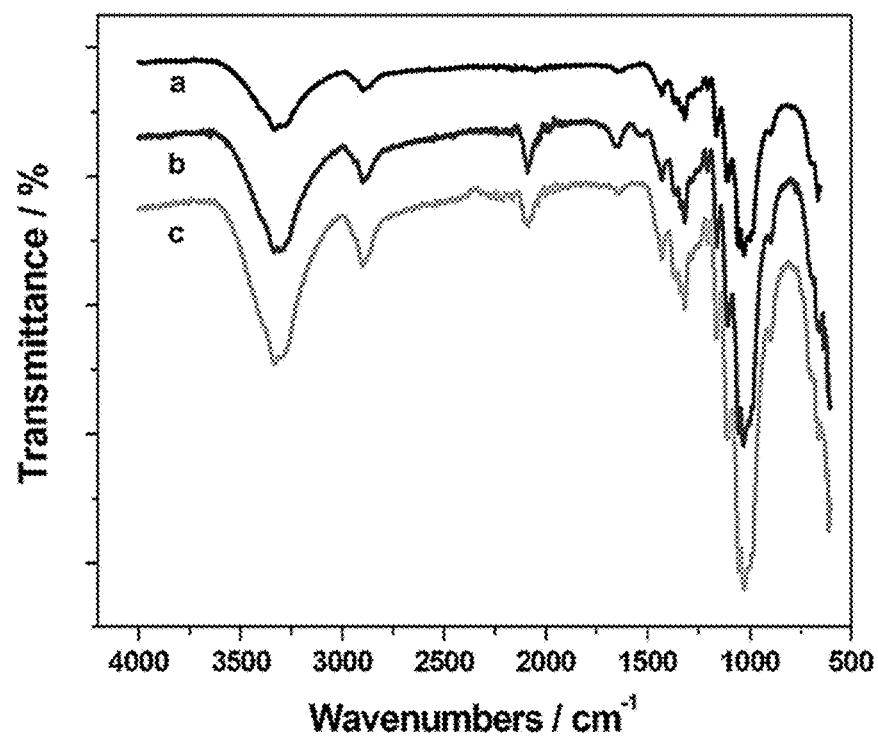
FIG. 14. FTIR of the immunoassay solution obtained from 32.0 ng·mL$^{-1}$ PSA. (a) Before and (b) after the reaction with potassium ferrocyanide. (c) FTIR of PB NPs.
FIG. 15. Photothermal immunoassay of PSA in spiked human serum samples (n=4).

Fourier transform infrared spectroscopy (FTIR) was performed to characterize the change of nanoparticles in the immunoassay solution at a PSA concentration of 32.0 ng·mL$^{-1}$ before and after the nanoparticle transformation process. An obvious stretching band was observed at 2085 cm$^{-1}$ (FIG. 14, *a*) in the FTIR spectrum of the immunoassay solution after the nanoparticle transformation process, while no band was observed before the process (FIG. 14, *b*). The stretching band corresponded well with that of PB NPs (FIG. 14, *c*) attributed to the CN stretching in the formed [Fe$^{II}$—CN—Fe$^{III}$] structure, indicating the presence of PB in the immunoassay solution after the nanoparticle transformation process.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An immunoassay for detecting or measuring an analyte contained in a sample, comprising:
   reacting the analyte with a binding reagent, the binding reagent capable of specifically binding the analyte and forming a binding reagent/analyte complex;
   contacting the binding reagent/analyte complex with a detection reagent comprising-an iron oxide nanoparticle reagent that specifically binds the binding reagent/analyte complex;
   contacting the iron oxide nanoparticle reagent with a detection solution comprising a photothermal agent precursor under conditions forming a photothermal agent, wherein the photothermal agent is oxidized TMB;
   irradiating the photothermal agent produced by a reaction catalyzed by the iron oxide nanoparticle with light having a wavelength that is absorbed by the photothermal agent and is converted to heat; and
   measuring temperature change associated with the light irradiation, wherein a temperature increase is proportional to the amount of iron oxide nanoparticle bound to the analyte; or
   measuring the analyte concentration through a colorimetric method.

2. The immunoassay of claim 1, wherein the binding reagent is an antibody or functional antibody fragment.

3. The immunoassay of claim 1, wherein the light has a wavelength between 500 nm and 1000 nm.

4. The immunoassay of claim 1, wherein the analyte is a protein, nucleic acid, metabolite, small molecule, fungus, virus, or bacterium.

5. The immunoassay of claim 1, wherein the analyte binding reagent is immobilized on a support.

6. The immunoassay of claim 5, wherein the support is a microchip, tube, bead, or microarray.

7. The immunoassay of claim 1, wherein the sample is a biological sample.

* * * * *